(12) United States Patent
Thudium et al.

(10) Patent No.: US 6,893,840 B2
(45) Date of Patent: May 17, 2005

(54) CYTOMEGALOVIRUS INTRON A FRAGMENTS

(75) Inventors: Kent B. Thudium, Oakland, CA (US); Mark Selby, San Francisco, CA (US)

(73) Assignee: Chiron Corporation, Emeryville, CA (US)

( * ) Notice: Subject to any disclaimer, the term of this patent is extended or adjusted under 35 U.S.C. 154(b) by 19 days.

(21) Appl. No.: 09/977,066

(22) Filed: Oct. 12, 2001

(65) Prior Publication Data

US 2005/0079488 A1 Apr. 14, 2005

Related U.S. Application Data

(60) Provisional application No. 60/240,502, filed on Oct. 13, 2000.

(51) Int. Cl.$^7$ .......................... C12P 21/06; C12N 15/00; C12N 5/00; C12Q 1/68; C07H 21/04
(52) U.S. Cl. ...................... 435/69.1; 435/320.1; 435/6; 435/325; 435/252.3; 435/257.2; 536/24.1; 536/24.2
(58) Field of Search ........................ 435/69.1, 6, 320.1, 435/325, 440, 377, 455; 536/24.1, 24.2

(56) References Cited

U.S. PATENT DOCUMENTS

| | | | |
|---|---|---|---|
| 5,688,688 A | 11/1997 | Luciw et al. | |
| 5,739,018 A | 4/1998 | Miyanohara et al. | |
| 6,251,872 B1 | 6/2001 | Barbet et al. | ................. 514/44 |

FOREIGN PATENT DOCUMENTS

| | | |
|---|---|---|
| WO | WO 96/32932 | 10/1996 |
| WO | WO 00/41679 | 7/2000 |
| WO | WO 91/02607 | 1/2001 |

OTHER PUBLICATIONS

Montgomery et al., "Heterologous and Homologous Protection Against Influenza A by DNA Vaccination: Optimization of DNA Vectors" *DNA and Cell Biology* 12(9):777–783, 1993.

Wagener et al., "Induction of Antibodies Against SIV Antigens After Intramuscular Nucleic Acid Inoculation Using Complex Expression Constructs" *Journal of Biotechnology* 44:59–65, 1996.

Murphey–Corb et al., "Induction of Immunodeficiency Virus–Specific Immune Responses in Rehesus Monkeys Following Gene Gun–Mediated DNA Vaccination" *J. Med. Primatol.* 25:236–241, 1996.

Norman et al., "Development of Improved Vectors for DNA–Based Immunization and Other Gene Therapy Applications" *Vaccine* 15(8):801–803, 1997.

Ramasamy et al., "Mammalian Cell Expression of Malaria Merozoite Surface Proteins and Experimental DNA and RNA Immunisation" *Biochimica et Biophysica Acta* 1453:1–13, 1999.

Little–van den Hurk et al., "Intradermal Immunization with a Bovine Herpesvirus–1 DNA Vaccine Induces Protective Immunity in Cattle" *J. General Virology* 79:831–839, 1998.

Little–van den Hurk et al., "Immune Responses and Protection Induced by DNA Vaccines Encoding Bovine Parainfluenza Virus Type 3 Glycoproteins" *Virology* 260:35–46, 1999.

Arulkanthan et al., "Biased Immunoqlobulin G1 Isotype Responses Induced in Cattle with DNA Expressing msp1a of *Anaplasma marginale*" *Infection and Immunity* 67(7):3481–3487, Jul., 1999.

Xu et al., "Optimization of Transcriptional Regulatory Elements for Constructing Plasmid Vectors" *Gene* 272:149–156, 2001.

Tonjes et al., "Expression of Human Endogenous Retrovirus Type K Envelope Glycoprotein in Insect and Mammalian Cells" *J. Virology* 71(4):2747–2756, Apr., 1997.

Tripathy et al., "Long–Term Expression of Erythropoietin in the Systemic Circulation of Mice After Intramuscular Injection of a Plasmid DNA Vector" *Proc. Natl. Acad. Sci. USA* 93:10876–10880, Oct., 1996.

Akrigg et al., "The Structure of the Major Immediate Early Gene of Human Cytomegalovirus Strain AD169," *Virus Research* 2:107–121 (1985).

Buchman et al., "Comparison of Intron–Dependent and Intron–Independent Gene Expression," *Molec. Cell. Biol.* 8:4395–4405 (1988).

Chapman et al., "Effect of Intron A From Human Cytomegalovirus (Towne) Immediate–Early Gene on Heterologous Expression in Mammalian Cells," *Nucleic Acids Research* 19:3979–3986 (1991).

Cullen B. R., "Connections Between the Processing and Nuclear Export of mRNA: Evidence for an Export License," *Proc. Natl. Acad. Sci. U.S.A.* 97(1):4–6 (1999).

Foecking and Hofstetter, "Powerful and Versatile Enhancer–Promoter Unit for Mammalian Expression Vectors," *Gene* 45:101–105 (1986).

Gorewit et al., "Growth Hormone Gene Expression in Myoepithelial Cells Directed by Various Eucaryotic Transcriptional Regulatory Sequences," *FEB* 225(1,2):238–242 (1987).

Luo et al., "Splicing is Required for Rapid and Efficient mRNA Export in Metazoans," *Proc. Natl. Acad Sci. U.S.A.* 96(26):14937–14942 (1999).

(Continued)

*Primary Examiner*—Gerry Leffers
*Assistant Examiner*—Maria Marvich
(74) *Attorney, Agent, or Firm*—Roberta L. Robins; Helen Lee; Alisa A. Harbin

(57) ABSTRACT

Cytomegalovirus (CMV) Intron A fragments for expressing gene products are disclosed. Also described are expression vectors including the fragments, as well as methods of using the same.

17 Claims, 6 Drawing Sheets

OTHER PUBLICATIONS

Mosca et al., "Novel Induction by Herpes Simplex Virus of Hybrid Interferon Gene Transcripts Driven by the Strong Cytomegalovirus IE94 Promoter," *Journal of Virology* 61(3):819–828 (1987).

Nelson et al., "Negative and Positive Regulation by a Short Segment in the 5'–Flanking Region of the Human Cytomegalovirus Major Immediate–Early Gene," *Molecular and Cellular Biology* 7(11):4125–4129 (1997).

Pasleau et al., "Growth Hormone Gene–Expression in Eukaryotic Cells Directed by the Rous Sarcoma Virus Long Terminal Repeat or Cytomegalovirus Immediate–Early Promoter," *Gene* 38:227–232 (1985).

Tevethia et al., "Participation of Two Human Cytomegalovirus Immediate Early Gene Regions in Transcriptional Activation of Adenovirus Promoters," *Virology* 161:276–285 (1987).

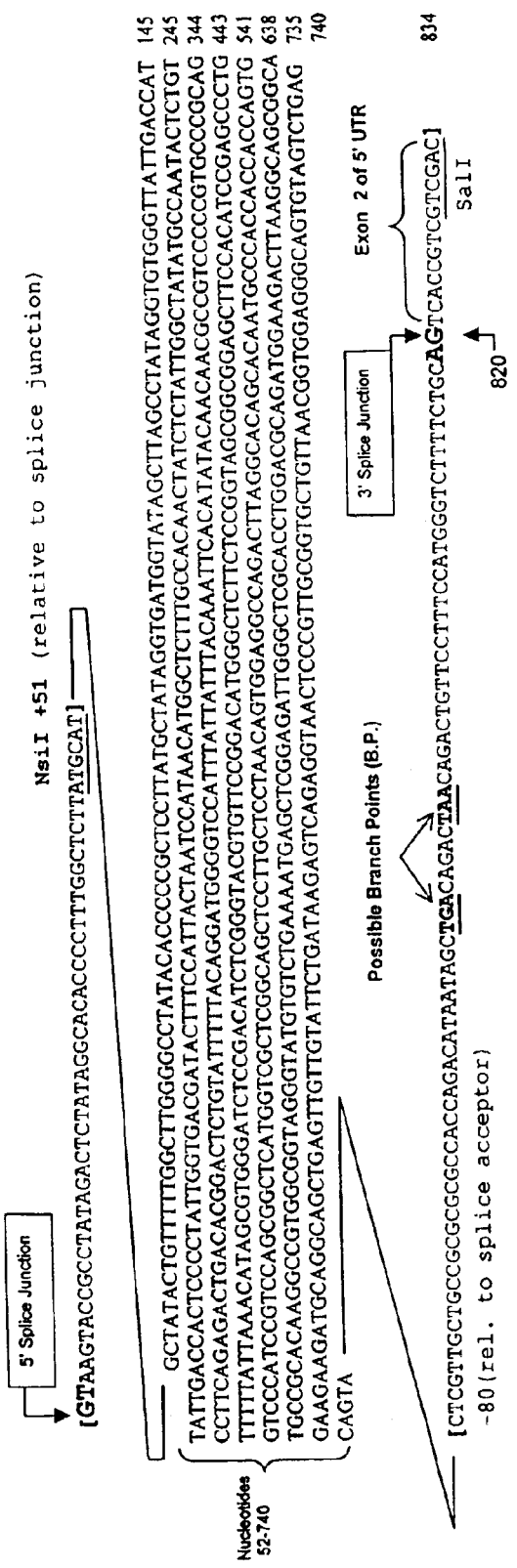

```
   1 ctgcagtgaa taataaaatg tgtgtttgtc cgaaatacgc gttttgagat ttctgtcgcc
  61 gactaaattc atgtcgcgcg atagtggtgt ttatcgccga tagagatggc gatattggaa
 121 aaatcgatat ttgaaaatat ggcatattga aaatgtcgcc gatgtgagtt tctgtgtaac
 181 tgatatcgcc atttttccaa aagtgatttt tgggcatacg cgatatctgg cgatacggct
 241 tatatcgttt acggggatg gcgatagacg actttggcga cttgggcgat tctgtgtgtc
 301 gcaaatatcg cagtttcgat ataggtgaca gacgatatga ggctatatcg ccgatagagg
 361 cgacatcaag ctggcacatg gccaatgcat atcgatctat acattgaatc aatattggca
 421 attagccata ttagtcattg gttatatagc ataaatcaat attggctatt ggccattgca
 481 tacgttgtat ctatatcata atatgtacat ttatattggc tcatgtccaa tatgaccgcc
 541 atgttgacat tgattattga ctagttatta atagtaatca attacgggt cattagttca
 601 tagcccatat atggagttcc gcgttacata acttacggta aatgcccgc ctcgtgaccg
 661 cccaacgacc cccgcccatt gacgtcaata atgacgtatg ttcccatagt aacgccaata
 721 gggactttcc attgacgtca atgggtggag tatttacggt aaactgccca cttggcagta
 781 catcaagtgt atcatatgcc aagtccggcc cctattgac gtcaatgacg gtaaatggcc
 841 cgcctggcat tatgcccagt acatgacctt acgggactt cctacttggc agtacatcta
 901 cgtattagtc atcgctatta ccatggtgat gcggttttgg cagtacacca atgggcgtgg
 961 atagcggttt gactcacggg gatttccaag tctccacccc attgacgtca atgggagttt
1021 gttttggcac caaaatcaac gggacttcc aaaatgtcgt aataacccg cccgttgac
1081 g caaat gggc ggtaggcgtg tacggtggga ggtcta tata a gcagagctc gtttagtgaa
         +1
1141 ccg t cagatc gcctggagac gccatccacg ctgttttgac ctccatagaa gacaccggga
1201 ccgatccagc ctccgcggcc gggaacggtg cattggaacg cggattcccc gtgccaagag
1261 tgacGTAAGT ACCGCCTATA GACTCTATAG GCACACCCCT TTGGCTCTTA TGCATGCTAT
1321 ACTGTTTTTG GCTTGGGGCC TATACACCCC CGCTCCTTAT GCTATAGGTG ATGGTATAGC
1381 TTAGCCTATA GGTGTGGGTT ATTGACCATT ATTGACCACT CCCCTATTGG TGACGATACT
1441 TTCCATTACT AATCCATAAC ATGGCTCTTT GCCACAACTA TCTCTATTGG CTATATGCCA
1501 ATACTCTGTC CTTCAGAGAC TGACACGGAC TCTGTATTTT TACAGGATGG GGTCCCATTT
1561 ATTATTTACA AATTCACATA TACAACAACG CCGTCCCCCG TGCCCGCAGT TTTTATTAAA
1621 CATAGCGTGG GATCTCCACG CGAATCTCGG GTACGTGTTC CGGACATGGG CTCTTCTCCG
1681 GTAGCGGCGG AGCTTCCACA TCCGAGCCCT GGTCCCATGC CTCCAGCGGC TCATGGTCGC
1741 TCGGCAGCTC CTTGCTCCTA ACAGTGGAGG CCAGACTTAG GCACAGCACA ATGCCCACCA
1801 CCACCAGTGT GCCGCACAAG GCCGTGGCGG TAGGGTATGT GTCTGAAAAT GAGCTCGGAG
1861 ATTGGGCTCG CACCGTGACG CAGATGGAAG ACTTAAGGCA GCGGCAGAAG AAGATGCAGG
1921 CAGCTGAGTT GTTGTATTCT GATAAGAGTC AGAGGTAACT CCCGTTGCGG TGCTGTTAAC
1981 GGTGGAGGGC AGTGTAGTCT GAGCAGTACT CGTTGCTGCC GCGCGCGCCA CCAGACATAA
2041 TAGCTGACAG ACTAACAGAC TGTTCCTTTC CATGGGTCTT TTCTGCAGtc accgtccttg
2101 acacgatgga gtcctctgcc aagagaaag a tg gaccctga taatcctgac gagggccctt
2161 cctccaaggt
```

Enhancer Region (~600 – ~1081)

Pol II Promoter (1081 – 1143)

Exon 1 (5' UTR) (1144 – 1264)

Intron A (1265 – 2088)

Exon 2 (5' UTR, Start of Trl.) (2089 – )

FIG. 2

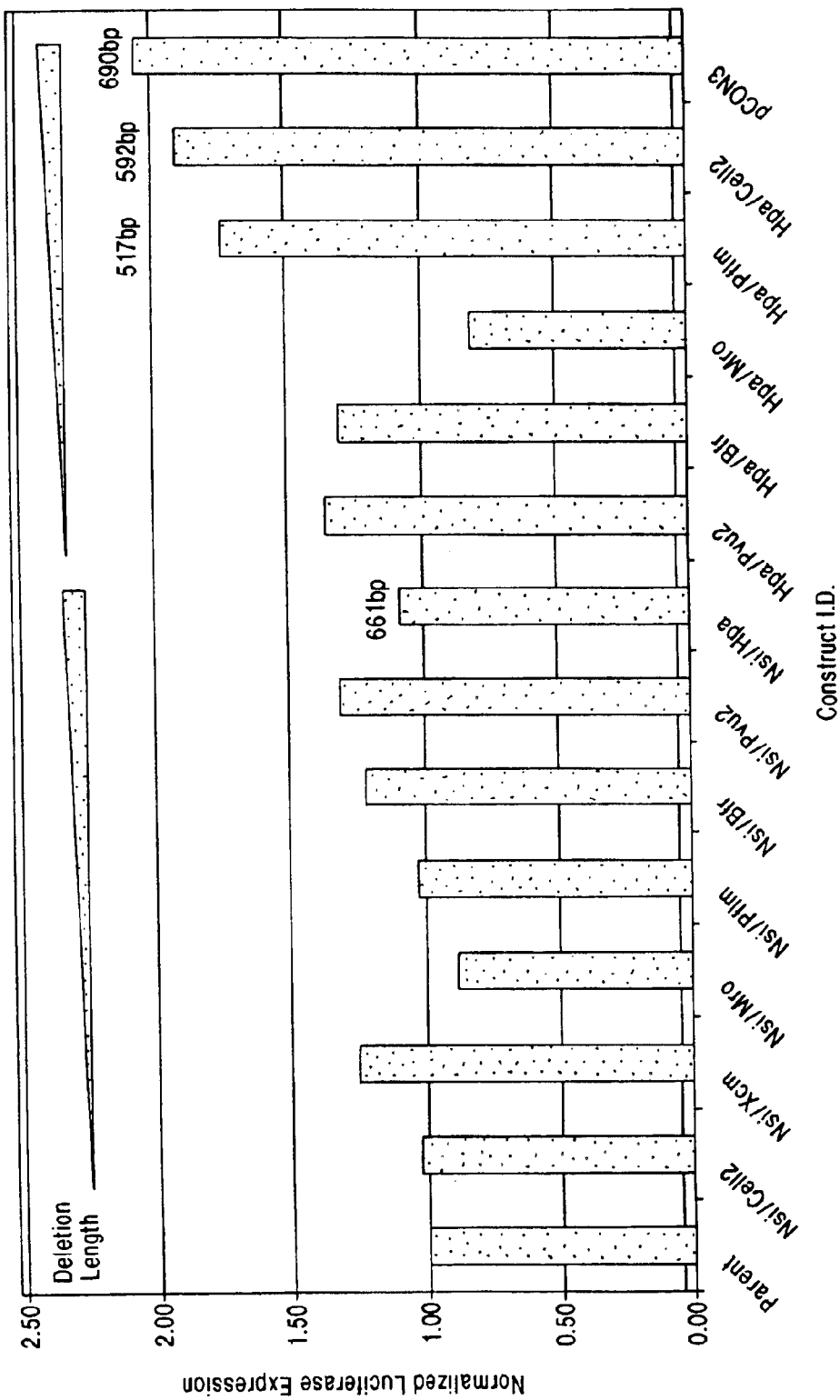

1. Wild Type Rabbit β-Globin Sequence
G̲T̲T̲G̲G̲T̲A̲T̲C̲CTTTTTACAGCACAACTTAATGAGACAGATAGAAACTGGTCTTGTAGAAACA
Splice Donor GAGTAGTCGCCTGCTTTTCTGCCAGGT̲G̲C̲T̲G̲A̲C̲TTCTCTCCCCT̲G̲G̲G̲C̲T̲G̲T̲T̲T̲T̲C̲A̲T̲T̲T̲T̲CTCAG
                                Branch Pt.          Polypyrimidine Tract

FIG. 5A

2. Optimized Rabbit β-Globin Sequence
G̲T̲A̲A̲G̲T̲A̲T̲C̲CTTTTTACAGCACAACTTAATGAGACAGATAGAAACTGGTCTTGTAGAAACA
Splice Donor GAGTAGTCGCCTGCTTTTCTGCCAGGT̲A̲C̲T̲A̲A̲C̲TTCTCTCCCCT̲C̲T̲C̲C̲T̲C̲T̲T̲T̲T̲C̲T̲T̲T̲T̲T̲CTGCAG
                                  Branch Pt.          Polypyrimidine Tract

FIG. 5B

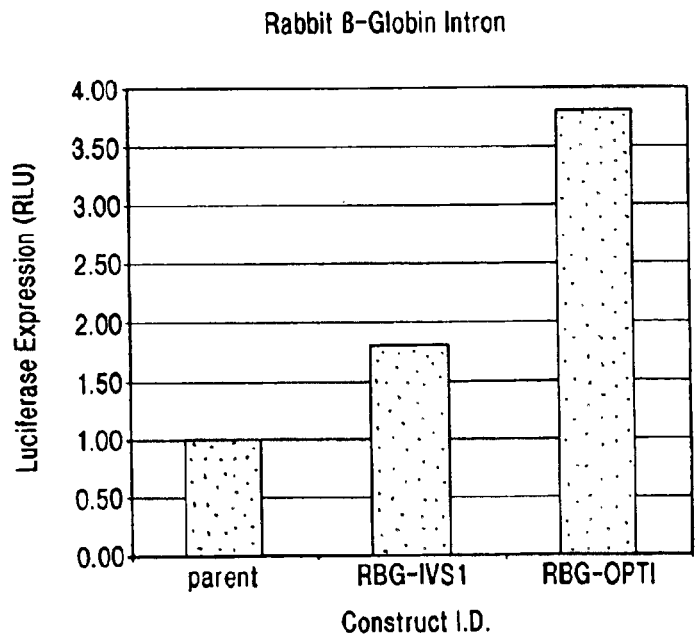

FIG. 6

CYTOMEGALOVIRUS INTRON A FRAGMENTS

CROSS-REFERENCE TO RELATED APPLICATIONS

This application is related to provisional patent application Ser. No. 60/240,502 filed Oct. 13, 2000, from which application priority is claimed under 35 USC §119(e)(1) and which application is incorporated herein by reference in its entirety.

TECHNICAL FIELD

The present invention relates generally to recombinant gene expression systems. More particularly, the invention relates to novel cytomegalovirus (CMV) Intron A fragments for use in expression constructs for expressing gene products, and methods of using the same.

BACKGROUND OF THE INVENTION

Proteins are conveniently produced in a variety of procaryotic and eucaryotic recombinant expression, systems. For example, *Eschericia coli*-derived plasmid DNA vectors are widely used to express proteins both in vitro and in vivo. In vitro, such vectors are used for purposes ranging from e.g., preliminary evaluation of the nature of protein expression to large-scale manufacture of recombinant proteins. In vivo, DNA vectors are used, for example, for gene therapy and nucleic acid vaccination.

In general, effective vectors are those that express high levels of protein due to the use of efficient promoters and other control elements. Other factors that may contribute to efficient transfection of cells include: (1) uptake of plasmid by cells; (2) escape of plasmid from endocytic vesicles after endocytosis; (3) translocation of the plasmid from the cytoplasm into the nucleus; and (4) transcription of the plasmid in the nucleus.

Work from several laboratories suggests that a major barrier to efficient transfection is translocation of the plasmid into the nucleus, particularly in cells that do not undergo mitosis (e.g., myocytes). One parameter that may affect this step is the size of the plasmid, as the nuclear pore complex involved in uptake of macromolecules into the nucleus has a finite size. Hence, it is desirable to engineer small plasmids that retain the ability to express proteins at high levels. This has the potential to facilitate DNA delivery and allows the insertion of larger gene inserts than is feasible in larger plasmids. The latter point is particularly important for preparation of certain recombinant viral vectors that have a limited capacity to package plasmids, such as alphavirus and adeno-associated vectors.

One particularly effective system for the production of recombinant proteins employs vectors containing the human cytomegalovirus (hCMV) immediate-early (IE1) enhancer/promoter region which controls transcription of the immediate-early 72,000 molecular weight protein of hCMV. See, e.g., Chapman et al., *Nuc. Acids Res.* (1991) 19:3979–3986; and U.S. Pat. No. 5,688,688. The hCMV IE1 enhancer/promoter is one of the strongest enhancer/promoters known and is active in a broad range of cell types.

The hCMV IE1 enhancer/promoter region (FIG. 2) includes a tissue-specific modulator, multiple potential binding sites for several different transcription factors, and a complex enhancer. The transcribed region of the gene contains four exons and three introns. The largest of the introns, termed "Intron A," is found within the 5'-untranslated region of the gene. See, e.g., Chapman et al., *Nuc. Acids Res.* (1991) 19:3979–3986 for the sequence and structure of this region in hCMV strain Towne, and Akrigg et al., *Virus Res.* (1985) 2:107–121, for a description of the corresponding region in hCMV strain AD169. The Intron A region of the hCMV IE1 enhancer/promoter has been shown to contain elements that enhance expression of heterologous proteins in mammalian cells. See, e.g., Chapman et al., *Nuc. Acids Res.* (1991) 19:3979–3986.

Introns are non-coding regions present in most pre-mRNA transcripts produced in the mammalian cell nucleus. Intron sequences can profoundly enhance gene expression when included in heterologous expression vectors. See, e.g., Buchman et al., *Molec. Cell. Biol.* (1988) 8:4395–4405; Chapman et al., *Nuc. Acids Res.* (1991) 19:3979–3986. Recent studies have demonstrated a connection between pre-mRNA splicing and export from the nucleus of mature mRNAs to the cytoplasm. Cullen, B. R., *Proc. Natl. Acad. Sci. USA* (2000) 97:4–6; and Luo et al., *Proc. Natl. Acad. Sci. USA* (1999) 96:14937–14942. Accordingly, increased levels of expression, such as those seen with the Intron A region of the hCMV IE1 enhancer/promoter, may be due to increased levels of translatable mRNAs in the cytoplasm.

SUMMARY OF THE INVENTION

Accordingly, the present invention provides CMV Intron A fragments for use in expression constructs. The fragments retain the ability to enhance expression levels when present in such expression constructs. The use of Intron A fragments is desirable, especially when used in recombinant viral vectors with size constraints for packaging plasmids, such as alphavirus and adeno-associated vectors. Thus, the present invention provides a highly efficient expression system for the production of recombinant proteins in therapeutically useful quantities, both in vitro and in vivo.

Accordingly, in one embodiment, the subject invention is directed to an hCMV Intron A fragment, wherein the fragment lacks the full-length Intron A sequence and comprises: (a) a sequence of nucleotides having at least about 75% sequence identity to the contiguous sequence of nucleotides found at positions 1–25, inclusive, of FIG. 1A, and (b) a sequence of nucleotides having at least about 75% sequence identity to the contiguous sequence of nucleotides found at positions 775–820, inclusive, of FIG. 1A. Further, when the fragment is present in an expression construct, the expression construct achieves expression levels greater than those levels achieved by a corresponding construct that completely lacks an Intron A sequence. In certain embodiments, the expression levels achieved are at least two-fold, or at least ten-fold, or at least fifty-fold greater than those levels achieved by a corresponding construct that completely lacks an Intron A sequence.

In another embodiment, the invention is directed to an Intron A fragment that comprises: (a) a sequence of nucleotides having at least about 75% sequence identity to the contiguous sequence of nucleotides found at positions 1–51, inclusive, of FIG. 1A, and (b) a sequence of nucleotides having at least about 75% sequence identity to the contiguous sequence of nucleotides found at positions 741–820, inclusive, of FIG. 1A, wherein when the fragment is present in an expression construct, the expression construct achieves expression levels greater than those levels achieved by a corresponding construct that completely lacks an Intron A sequence. In certain embodiments, the expression levels achieved are at least two-fold, or at least ten-fold, or at least fifty-fold greater than those levels achieved by a corresponding construct that completely lacks an Intron A sequence.

In another embodiment, the Intron A fragment comprises the sequence of nucleotides 1–51, inclusive, of FIG. 1A, linked to nucleotides 741–820, inclusive, of FIG. 1A.

In still a further embodiment, the Intron A fragment comprises the Intron A nucleotide sequence depicted in FIG. 1C, or a nucleotide sequence with at least about 75% sequence identity thereto.

In another embodiment, the Intron A fragment consists of the Intron A nucleotide sequence depicted in FIG. 1C.

In yet another embodiment, the invention is directed to an hCMV Intron A fragment, wherein the fragment lacks the full-length Intron A sequence and comprises: (a) a sequence of nucleotides having at least about 75% sequence identity to the contiguous sequence of nucleotides found at positions 1–25, inclusive, of FIG. 1A, and (b) a sequence of nucleotides having at least about 75% sequence identity to the contiguous sequence of nucleotides found at positions 775–820, inclusive, of FIG. 1A, wherein when the fragment is present in an expression construct, the expression construct achieves expression levels equal to, or greater than, those levels achieved by an expression construct that includes a corresponding intact, full-length Intron A sequence.

In another embodiment, the invention is directed to an hCMV Intron A fragment, wherein the fragment lacks the full-length Intron A sequence and comprises: (a) a sequence of nucleotides having at least about 75% sequence identity to the contiguous sequence of nucleotides found at positions 1–51, inclusive, of FIG. 1A, and (b) a sequence of nucleotides having at least about 75% sequence identity to the contiguous sequence of nucleotides found at positions 741–820, inclusive, of FIG. 1A, wherein when the fragment is present in an expression construct, the expression construct achieves expression levels equal to, or greater than, those levels achieved by an expression construct that includes a corresponding intact, full-length Intron A sequence.

In further embodiments, the invention is directed to recombinant expression constructs comprising (a) a coding sequence; and (b) control elements that are operably linked to the coding sequence, wherein the control elements comprise the Intron A fragment described herein, whereby the coding sequence can be transcribed and translated in a host cell. In certain embodiments, the control elements further comprise a promoter selected from the group consisting of an SV40 early promoter, a CMV promoter, a mouse mammary tumor virus LTR promoter, an adenovirus major late promoter, an RSV promoter, a SRα promoter, and a herpes simplex virus promoter. Particularly, the control elements may comprise the hCMV immediate-early (IE1) enhancer/promoter region found at nucleotide positions 460 to 1264 of FIG. 2, and Exon 2 of the 5'-UTR comprising the sequence of nucleotides depicted at positions 821–834, inclusive, of FIG. 1A. Host cells comprising the expression constructs and methods of producing a recombinant polypeptide are also provided.

In another embodiment, the invention is directed to a polynucleotide comprising the sequence depicted in FIG. 5B.

These and other aspects of the present invention will become evident upon reference to the following detailed description and attached drawings. In addition, various references are set forth herein which describe in more detail certain procedures or compositions, and are therefore incorporated by reference in their entirety.

BRIEF DESCRIPTION OF THE DRAWINGS

FIG. 1A (SEQ ID NO: 1) shows the sequence of a representative CMV IE1 Intron A from hCMV strain Towne. Also shown in FIG. 1A is the portion of the sequence deleted from deletion mutant pCON3. The splice donor sequence is bolded and shown with an arrow. The splice acceptor sequence is underlined and designated with an arrow. Possible branch points are indicated.

FIG. 1B (SEQ ID NO:2) shows the oligonucleotide corresponding to the retained 3'-portion of the deleted Intron A construct of pCON3 as compared with the 3'-portion of wild-type Intron A.

FIG. 1C (SEQ ID NO:3) shows the Intron A sequence of deletion mutant pCON3.

FIG. 2 (SEQ ID NO:4) (GenBank accession number M60321 and Chapman et al., Nuc. Acids Res. (1991) 19:3979–3986) shows the nucleotide sequence of the 5' region of the major immediate-early gene of hCMV, including the enhancer/promoter region. The enhancer region (nucleotides ~600 to ~1081), the Pol II promoter (nucleotides 1081–1143), Exon 1 of the 5' UTR (nucleotides 1144–1264), Intron A (nucleotides 1265–2088) and Exon 2 of the 5' UTR (nucleotides 2089–2096) are shown. The TATAA and CAAT boxes, as well as the start codon, are boxed.

FIG. 4 depicts normalized luciferase expression by the various deletion mutants shown in FIG. 1C and FIG. 3.

FIG. 5A (SEQ ID NO:5) shows the wild-type rabbit β-globin gene sequence used in the examples.

FIG. 5B (SEQ ID NO:6) shows the optimized rabbit β-globin gene sequence used in the examples.

FIG. 6 shows luciferase expression as a measure of p55gag expression by parent vector, pCMVkm-Luciferase, as compared to RβG-IVSI (containing the wild-type rabbit β-globin gene sequence shown in FIG. 4A) and RβG-OPTI (containing the optimized rabbit β-globin gene sequence shown in FIG. 4B)

DETAILED DESCRIPTION OF THE INVENTION

Figure 3:
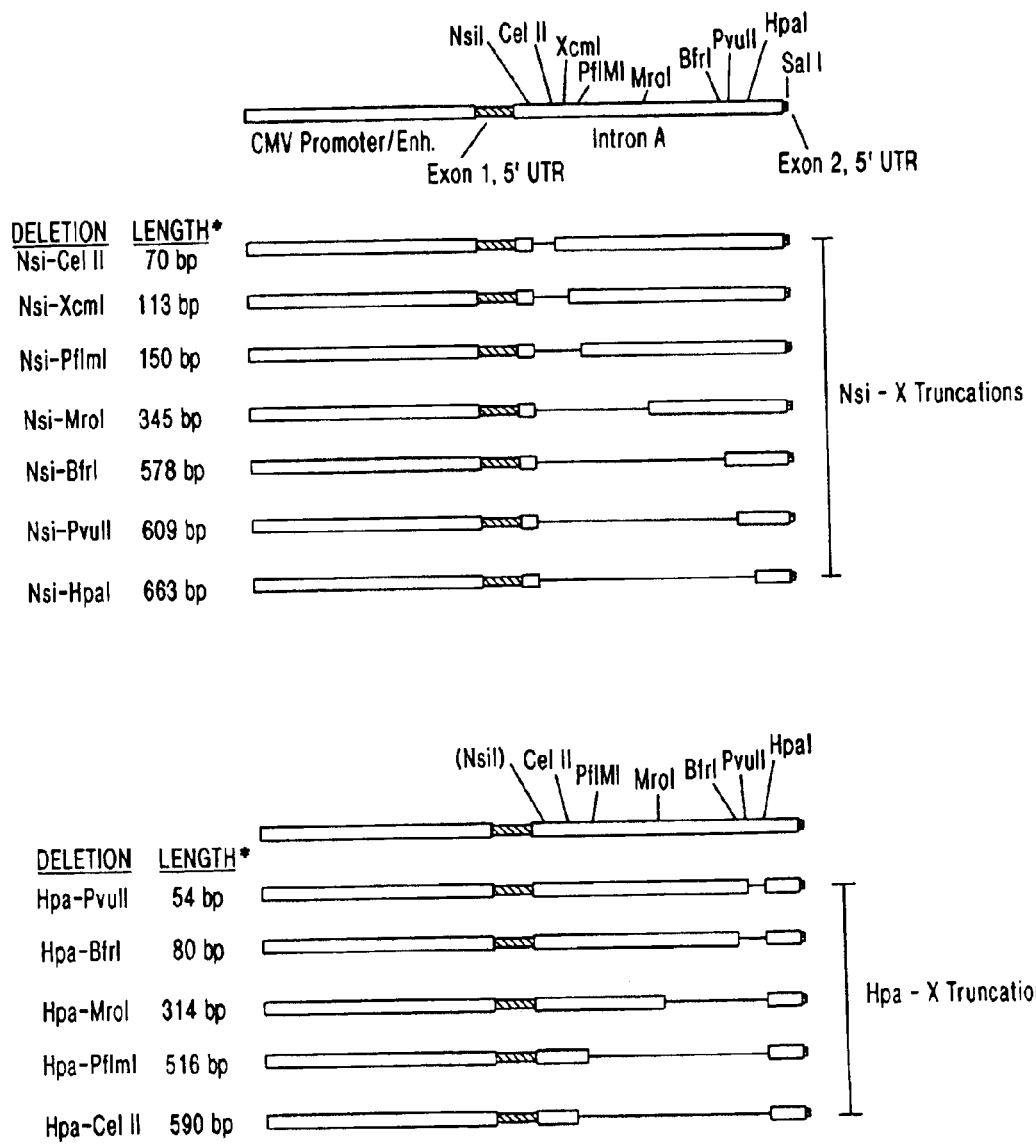
FIG. 3 shows various Intron A deletion mutants as described in the examples.

The practice of the present invention will employ, unless otherwise indicated, conventional methods of chemistry, biochemistry, recombinant DNA techniques and immunology, within the skill of the art. Such techniques are explained fully in the literature. See, e.g., Sambrook, et al., *Molecular Cloning: A Laboratory Manual* (2nd Edition); *Methods In Enzymology* (S. Colowick and N. Kaplan eds., Academic Press, Inc.); *DNA Cloning*, Vols. I and II (D. N. Glover ed.); *Oligonucleotide Synthesis* (M. J. Gait ed.); *Nucleic Acid Hybridization* (B. D. Hames & S. J. Higgins eds.); *Animal Cell Culture* (R. K. Freshney ed.); Perbal, B., *A Practical Guide to Molecular Cloning*.

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "an antigen" includes a mixture of two or more antigens, and the like.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid; Glu (E) | Glycine; Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

I. Definitions

In describing the present invention, the following terms will be employed, and are intended to be defined as indicated below.

By "Intron A fragment" is meant a fragment derived from an Intron A sequence of a CMV immediate-early enhancer/promoter region, which does not include the entire Intron A sequence. A representative hCMV enhancer/promoter region is shown in FIG. 2. The intact Intron A sequence is represented by the lowercase nucleotides spanning positions 1265–2088 of FIG. 2 and nucleotides 1–820 of FIG. 1A. The Intron A fragment of the present invention comprises a deletion from the full-length sequence, which deletion may be internal or occur at the 5'- and/or 3'-ends of the Intron A region, so long as the region still functions to permit authentic splicing in the nucleus of primary transcripts that include the Intron A fragment. Preferably, an "Intron A fragment" includes the minimum number of bases or elements necessary to achieve expression levels over those achieved in corresponding constructs that completely lack an Intron A sequence. More preferably, expression levels achieved by constructs that include the Intron A fragment of the invention are at least two-fold over those levels achieved without the presence of the Intron A region, preferably at least ten-fold greater, most preferably at least twenty- to fifty-fold greater, or more, than those levels achieved without the Intron A region. Preferably, expression levels are at least equal to, or greater than, for example at least two-fold greater than, those levels achieved when the intact, full-length Intron A sequence is present in a corresponding expression construct. Such comparisons are typically made by making expression constructs that include all elements of the test construct, but either completely lack the Intron A sequence, or include the full-length Intron A sequence (see the Examples herein).

Thus, an "Intron A fragment" of the present invention will generally include at least the 5' splice junction sequence (nucleotides 1–7 as shown in FIG. 1A), usually at least up to the first 25 5'-nucleotides of the Intron A region (nucleotides 1–25 of FIG. 1A), more preferably at least up to the first 30 nucleotides of the Intron A region (nucleotides 1–30 of FIG. 1A), even more preferably at least up to the first 40 nucleotides of the Intron A region (nucleotides 1–40 of FIG. 1A), more preferably at least up to the first 51 nucleotides of the Intron A region (nucleotides 1–51 of FIG. 1A), and even up to the first 75 or more nucleotides of the Intron A region, and any integer between these values, or even more of the 5'-region of Intron A.

Moreover, in addition to the 5'-sequence described above, an "Intron A fragment" will optionally include at least the 3' splice junction sequence (nucleotides 815–820 of FIG. 1A). Generally, the Intron A fragment will include at least up to the 25 3'-nucleotides of the Intron A sequence shown in FIG. 1A (nucleotides 796–820 of FIG. 1A), preferably up to the 50 3'-nucleotides of the sequence shown in FIG. 1A (nucleotides 771–820 of FIG. 1A), more generally up to the 70 3'-nucleotides (nucleotides 751–820 of FIG. 1A), preferably at least up to the 80 3'-nucleotides (nucleotides 741–820 of FIG. 1A), or even more of the 3'-region, such as the 100–150 3'-nucleotides, and any integer between these values, or more of the 3'-region of Intron A.

Thus, it is apparent that an Intron A fragment according to the present invention may include a variety of internal deletions, such as about 10 to about 750 or more nucleotides of the Intron A sequence, preferably about 25 to about 700 or more nucleotides, more preferably about 50 to about 700 nucleotides, and most preferably about 500 to about 680–690 or more nucleotides, or any integer between the above ranges, so long as an expression construct including the Intron A fragment either enhances expression relative to a corresponding construct completely lacking an Intron A sequence, or provides equivalent or enhanced expression relative to a corresponding construct which includes the entire Intron A sequence, as described above.

The retained 5'- and 3'-regions of the Intron A fragment of the present invention may be directly linked to one another, e.g., as shown in FIG. 1A, or the 5'- and 3'-regions of the Intron A fragment may be linked together via a linker sequence. The linker sequence may comprise from 1 up to about 400 or more nucleotides, or any integer between these values, and may comprise regions for particular transcript factors, such as NF1 binding sites, tissue-specific enhancer sequences, such as muscle-specific enhancers, and the like.

One representative Intron A fragment sequence comprises the sequence of nucleotides at positions 1–51 linked to nucleotides 741–820, of FIG. 1A, thus comprising an internal deletion of nucleotides 52–740, as shown in FIG. 1A. Also included in this construct is Exon 2 of the 5' UTR of the hCMV enhancer/promoter region, nucleotides 821–834 of FIG. 1A.

An "Intron A fragment" as used herein, encompasses sequences with identity to an Intron A fragment isolated from any of the various hCMV strains, such as for example hCMV strain Towne and hCMV strain AD169, as well as polynucleotides that are substantially homologous to the reference molecule (as defined below) and which still function as described above. Thus, for example, the fragment shown in FIG. 1C includes nucleotide substitutions at the branch points and in the polypyrimidine tract to conform these sequences to consensus sequences, as shown in FIGS. 1B and 1C. Preferably, but not necessarily, the branch points retain termination codons, i.e., TAA, TAG or TGA. Moreover, portions of the molecule outside of the splice donor and splice acceptor regions are more amenable to change. In this regard, it is preferable to retain the 5' GT found at the 5' splice junction, and preferably the first six base pairs found at the 5' splice junction. It is also preferable to retain the 3' AG found at the 3' splice junction, preferably the three base pairs, CAG, found at the 3' splice junction. The nucleotides found in these regions are preferably at least 80% homologous to the sequence of nucleotides present in the native sequence shown in FIG. 1A, but may be less homologous as long as the Intron A fragment retains function, as defined above. Further, the polypyrimidine tract region is preferably one where substantially all of the bases are Ts or Cs.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like.

For purposes of the present invention, the polypeptide expressed by the coding sequence may be one useful in a vaccine, therapeutic or diagnostic and may be derived from any of several known viruses, bacteria, parasites and fungi, as well as any of the various tumor antigens. Alternatively, the expressed polypeptide may be a therapeutic hormone, a transcription or translation mediator, an enzyme, an intermediate in a metabolic pathway, an immunomodulator, and the like.

Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be serendipitous, such as through mutations of hosts which produce the proteins or errors due to PCR amplification.

A "coding sequence" or a sequence which "encodes" a selected polypeptide, is a nucleic acid molecule which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral (e.g. DNA viruses and retroviruses) or procaryotic DNA, and synthetic DNA sequences. A transcription termination sequence may be located 3' to the coding sequence.

A "nucleic acid" molecule can include both double- and single-stranded sequences and refers to, but is not limited to, cDNA from viral, procaryotic or eucaryotic mRNA, genomic DNA sequences from viral (e.g. DNA viruses and retroviruses) or procaryotic DNA, and especially synthetic DNA sequences. The term also captures sequences that include any of the known base analogs of DNA and RNA.

"Operably linked" refers to an arrangement of elements wherein the components so described are configured so as to perform their desired function. Thus, a given promoter operably linked to a coding sequence is capable of effecting the expression of the coding sequence when the proper transcription factors, etc., are present. The promoter need not be contiguous with the coding sequence, so long as it functions to direct the expression thereof. Thus, for example, intervening untranslated yet transcribed sequences can be present between the promoter sequence and the coding sequence, as can transcribed introns, and the promoter sequence can still be considered "operably linked" to the coding sequence.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

A "control element" refers to a polynucleotide sequence which aids in the expression of a coding sequence to which it is linked. The term includes promoters, transcription termination sequences, upstream regulatory domains, polyadenylation signals, untranslated regions, including 5'-UTRs (such as Exon 2 of the hCMV enhancer/promoter region 5'-UTR) and 3'-UTRs and when appropriate, leader sequences and enhancers, which collectively provide for the transcription and translation of a coding sequence in a host cell.

A "promoter" as used herein is a DNA regulatory region capable of binding RNA polymerase in a host cell and initiating transcription of a downstream (3' direction) coding sequence operably linked thereto. For purposes of the present invention, a promoter sequence includes the minimum number of bases or elements necessary to initiate transcription of a gene of interest at levels detectable above background. Within the promoter sequence is a transcription initiation site, as well as protein binding domains (consensus sequences) responsible for the binding of RNA polymerase. Eucaryotic promoters will often, but not always, contain "1TATAA" boxes and "CAAT" boxes.

A control sequence "directs the transcription" of a coding sequence in a cell when RNA polymerase will bind the promoter sequence and transcribe the coding sequence into mRNA, which is then translated into the polypeptide encoded by the coding sequence.

A "host cell" is a cell which has been transformed, or is capable of transformation, by an exogenous DNA sequence.

A "heterologous" region of a DNA construct is an identifiable segment of DNA within or attached to another DNA molecule that is not found in association with the other molecule in nature. For example, a sequence encoding a human protein other than the immediate-early 72,000 molecular weight protein of hCMV is considered a heterologous sequence when linked to an hCMV IE1 enhancer/promoter. Similarly, a sequence encoding the immediate-early 72,000 molecular weight protein of hCMV will be considered heterologous when linked to an hCMV promoter with which it is not normally associated. Another example of a heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

By "selectable marker" is meant a gene which confers a phenotype on a cell expressing the marker, such that the cell can be identified under appropriate conditions. Generally, a selectable marker allows selection of transected cells based on their ability to thrive in the presence or absence of a chemical or other agent that inhibits an essential cell function. Suitable markers, therefore, include genes coding for proteins which confer drug resistance or sensitivity thereto, impart color to, or change the antigenic characteristics of those cells transfected with a nucleic acid element containing the selectable marker when the cells are grown in an appropriate selective medium. For example, selectable markers include: cytotoxic markers and drug resistance markers, whereby cells are selected by their ability to grow on media containing one or more of the cytotoxins or drugs; auxotrophic markers by which cells are selected by their ability to grow on defined media with or without particular nutrients or supplements, such as thymidine and hypoxanthine; metabolic markers by which cells are selected for, e.g., their ability to grow on defined media containing the appropriate sugar as the sole carbon source, or markers which confer the ability of cells to form colored colonies on chromogenic substrates or cause cells to fluoresce. Representative selectable markers are described in more detail below.

"Expression cassette" or "expression construct" refers to an assembly which is capable of directing the expression of the sequence(s) or gene(s) of interest. The expression cassette includes control elements, as described above, such as a promoter or promoter/enhancer (such as the hCMV IE1 enhancer/promoter) which is operably linked to (so as to direct transcription of) the sequence(s) or gene(s) of interest, and often includes a polyadenylation sequence as well. An expression cassette will also include an Intron A fragment as defined above and, optionally, Exon 2 of the hCMV IE1 enhancer/promoter region. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

"Transformation," as used herein, refers to the insertion of an exogenous polynucleotide into a host cell, irrespective of the method used for insertion: for example, transformation by direct uptake, transfection, infection, and the like. For particular methods of transfection, see further below. The exogenous polynucleotide may be maintained as a nonintegrated vector, for example, an episome, or alternatively, may be integrated into the host genome.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

"Homology" refers to the percent identity between two polynucleotide or two polypeptide moieties. Two DNA, or two polypeptide sequences are "substantially homologous" to each other when the sequences exhibit at least about 50%, preferably at least about 75%, more preferably at least about 80%–85% (80, 81, 82, 83, 84, 85%), preferably at least about 90%, and most preferably at least about 95%–98% (95, 96, 97, 98%), or more, or any integer within the range of 50% to 100%, sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353–358, National biomedical Research Foundation, Washington, D.C., which adapts the local homology algorithm of Smith and Waterman *Advances in Appl. Math.* 2:482–489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix= BLOSUM62; Descriptions=50 sequences; sort by=HIGH SCORE; Databases=non-redundant, GenBank+EMBL+ DDBJ+PDB+GenBank CDS translations+Swiss protein+ Spupdate+PIR.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

II. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of compositions and methods similar or equivalent to those described herein can be used in the practice of the present invention, the preferred materials and methods are described herein.

As noted above, the present invention is based on the discovery of novel hCMV Intron A fragments which are able to enhance expression of a downstream (3') sequence relative to expression levels achieved in the absence of an Intron A sequence, or at least provide for equivalent expression levels as those obtained using the intact, full-length Intron A sequence. As explained above, the hCMV IE1 enhancer/promoter from which the Intron A sequence is derived, is one of the strongest enhancer/promoters known and is active in abroad range of cell types. See, e.g., Chapman et al., *Nuc. Acids Res.* (1991) 19:3979–3986; and U.S. Pat. No. 5,688,688. The use of active fragments from this region effectively reduces the overall plasmid size for expression of a particular coding sequence. This is particularly desirable when large coding sequences, and/or viral vectors with limited ability to package large genes, are used. Moreover, the decrease in overall size of the constructs effectively enhances efficiency of expression. Thus, the Intron A fragments of the present invention surprisingly retain the ability to result in expression of protein at high levels in vitro and in vivo and, in some cases, provide for higher expression than vectors using the entire hCMV IE1 Intron A sequence. As shown in the examples, these high levels of expression have provided for immune responses that are comparable to, or even better than, that induced by the parent vector.

As explained above, the Intron A fragments for use herein will retain at least up to the initial 7 nucleotides of the Intron A region, preferably at least up to the initial 25 nucleotides of the Intron A region (see, FIG. 1A for a representative Intron A sequence). In general, the Intron A fragment of the present invention will retain at least up to the first 30 nucleotides of the Intron A region (nucleotides 1–30 of FIG. 1A), generally at least up to the first 40 nucleotides of the Intron A region (nucleotides 1–40 of FIG. 1A), more preferably at least up to the first 51 nucleotides of the Intron A region (nucleotides 1–51 of FIG. 1A), and even up to the first 75 or more nucleotides of the Intron A region. Thus, the 5'-region may include 25, 26, 27, 28, 29, 30 . . . 50, 51, 52, 53, 54, 55 . . . 70, 71, 72, 73, 74, 75 . . . 85, 86, 87 or more of the 5'-nucleotides, and so on. It is evident that any number of nucleotides specified above, as well as nucleotides falling within the specified numbers, are intended to be encompassed herein, so long as an expression construct containing the Intron A fragment functions as defined above.

The Intron A fragment will optionally also include a sufficient amount of the 3'-region of Intron A to function as described herein. Generally, then, the Intron A fragment will include at least the 3' splice junction sequence (nucleotides 815–820 of FIG. 1A), preferably, at least up to the 25 3'-nucleotides of the Intron A sequence shown in FIG. 1A (nucleotides 796–820 of FIG. 1A), preferably up to the 50 3'-nucleotides of the sequence shown in FIG. 1A (nucleotides 771–820 of FIG. 1A), more generally up to the 70 3'-nucleotides (nucleotides 751–820 of FIG. 1A), preferably at least up to the 80 3'-nucleotides (nucleotides 741–820 of FIG. 1A), or even more of the 3'-region, such as the 100–150 3'-nucleotides, and any integer between these values, or more of the 3'-region of Intron A. Thus, the 3'-portion of the Intron A fragment may include 50, 51, 52, 53, 54, 55 . . . 70, 71, 72, 73, 74, 75 . . . 85, 86, 87 . . . 90, 92, 93, 94, 95, 96 . . . 110, 111, 112, and soon, or more of the 3'-nucleotides of the Intron A region. It is evident that any number of nucleotides specified above, as well as nucleotides falling within the specified numbers, are intended to be encompassed herein.

The 5'- and 3'-retained regions of the Intron A fragment of the present invention may be directly linked to one another, e.g., there may be an internal deletion of the Intron A sequence. This deletion may comprise, for example, 10–750 or more base pairs of the intact Intron A region, preferably about 300–700 base pairs, and most preferably about 500–700 base pairs. As shown in FIG. 1A, one preferable fragment includes a large internal deletion of about 688 base pairs. This fragment therefore includes the sequence of nucleotides at positions 1–51 directly linked to nucleotides 741–834, of FIG. 1A, thus comprising an internal deletion of nucleotides 52–740 of Intron A, as shown in FIG. 1A. Nucleotides 821–834 of FIG. 1A represent Exon 2 of the 5'-UTR. FIG. 3 shows various Intron A fragment constructs with Intron A deletions ranging from 55 to 661 base pairs.

Alternatively, the 5'- and 3'-regions of the Intron A fragment may be linked together via a linker sequence. The linker sequence may comprise from 1 up to about 400 or more nucleotides, preferably from 10–100 nucleotides, or any integer between these values, and may comprise regions for enhancers, particular transcript factors, such as NF1 binding sites, and the like.

The Intron A fragment of the present invention can be isolated from a CMV genomic library, as well as from plasmids containing the Intron A region, using an appropriate prffobe and cloned for future use. Similarly, the sequence can be produced synthetically, using known methods of polynucleotide synthesis (see, e.g. Edge, M. D., *Nature* (1981) 292:756; Nambair, et al. *Science* (1984) 223:1299; Jay, Ernest, J. Biol. Chem. (1984) 259:6311), based on the known Intron A sequence. See, e.g., Chapman et al., *Nuc. Acids Res.* (1991) 19:3979–3986 for the sequence and structure of the Intron A region in hCMV strain Towne, and Akrigg et al., *Virus Res.* (1985) 2:107–121, for a description of the corresponding region in hCMV strain AD169; and FIGS. 1A and 1C herein.

One particularly convenient method for obtaining the Intron A fragment of the present invention is to isolate Intron A (either alone, or in association with the rest of the hCMV enhancer/promoter region) from any of the various plasmids known to contain the same, using techniques well known in the art, as well as described in the examples herein. In particular, hCMV Intron A can be obtained from plasmid pCMV6, as described in Chapman et al., *Nuc. Acids Res.* (1991) 19:3979–3986 and U.S. Pat. No. 5,688,688, incorporated herein by reference in its entirety. Once obtained, the Intron A sequence can be manipulated to obtain deletion mutants thereof, such as by excising portions of the Intron A sequence using restriction enzymes. Site specific DNA cleavage is performed by treatment with a suitable restriction enzyme (or enzymes), under conditions which are generally understood in the art, and the particulars of which are specified by the manufacturer of these commercially available enzymes. See, e.g., New England Biolabs, Product Catalog. For example, restriction endonucleases with various specificities have been isolated from a wide range of prokaryotes and are well known in the art. See, e.g., Sambrook et al., supra. The choice of an appropriate restriction endonuclease depends on the particular sequence targeted. One of skill in the art will readily recognize the proper restriction enzyme to use for a desired sequence. If desired, size separation of the cleaved fragments may be performed by polyacrylamide gel or agarose gel electrophoresis, using standard techniques. A general description of size separations is found in, e.g., Sambrook et al., supra. The Intron A sequence can then be ligated to other control sequences such as an appropriate promoter (if the Intron A is isolated without the remaining hCMV IE1 enhancer/promoter region), and the desired coding sequence, using known techniques.

The sequence of the Intron A fragment can be optimized for use in particular expression systems using techniques well known in the art. Additionally, portions of the sequence of the fragment may be changed, e.g., by deleting or substituting possible branch points, as well as other regions of the molecule. These regions of a representative Intron A are shown in FIG. 1A. One particular optimized sequence of the Intron A fragment is shown in FIG. 1C. As explained in the examples, this fragment was obtained by first deleting most of the 3'-sequence of the Intron A region and then substituting, by means of a synthetic oligonucleotide, the last 80 nucleotides of the Intron A region with an optimized sequence, and including Exon 2 of the 5'-UTR region. The optimized sequence was based on published branch point and polypyrimidine track consensus sequences. Alternatively, mutagenized sequences can be obtained by techniques well known in the art, such as site-directed mutagenesis and polymerase chain reaction (PCR) techniques where appropriate. See, e.g., Sambrook, supra.

Once obtained, the fragment can be used to direct the transcription of a desired protein in a wide variety of cell types. C is-acting control elements can be conveniently associated with the Intron A fragment in order to optimize expression of the coding sequence associated therewith. If proteins produced in the system are either naturally secreted or engineered to be, the transformed cells may produce the protein product for protracted time periods, further increasing yields. The system allows for the production of a desired protein in an authentic configuration, with authentic post-translation modifications, in a relatively pure form and in economically useful amounts.

Thus, the Intron A fragments of the present invention will find use in expression constructs to express a wide variety of substances, including peptides which act as antibiotics and antiviral agents, e.g., immunogenic peptides for use in vaccines and diagnostics; recombinant antibodies; antineoplastics; immunomodulators, such as any of the various cytokines including interleukin-1, interleukin-2, interleukin-3, interleukin-4, and gamma-interferon; peptide hormones such as insulin, proinsulin, growth hormone, GHRH, LHRH, EGF, somatostatin, SNX-111, BNP, insulinotropin, ANP, FSH, LH, PSH and hCG, gonadal steroid hormones (androgens, estrogens and progesterone), thyroid-stimulating hormone, inhibin, cholecystokinin, ACTH, CRF, dynorphins, endorphins, endothelin, fibronectin fragments, galanin, gastrin, insulinotropin, glucagon, GTP-binding protein fragments, guanylin, the leukokinins, magainin, mastoparans, dermaseptin, systemin, neuromedins, neurotensin, pancreastatin, pancreatic polypeptide, substance P, secretin, thymosin, and the like; and growth factors, such as PDGF, EGF, KGF, IGF-1 and IGF-2, FGF, and the like.

More particularly, proteins for use in vaccines and diagnostics may be of viral, bacterial, fungal or parasitic origin, including but not limited to, those encoded by human and animal viruses and can correspond to either structural or non-structural proteins. For example, the present system will find use for recombinantly producing a wide variety of proteins from the herpesvirus family, including proteins derived from herpes simplex virus (HSV) types 1 and 2, such as HSV-I and HSV-2 glycoproteins gB, gD and gH; proteins derived from varicella zoster virus (VZV), Epstein-Barr virus (EBV) and cytomegalovirus (CMV) including CMV gB and gH; and proteins derived from other human herpesviruses such as HHV6 and HHV7. (See, e.g. Chee et al., *Cytomegaloviruses* (J. K. McDougall, ed., Springer-Verlag 1990) pp. 125–169, for a review of the protein coding content of cytomegalovirus; McGeoch et al., *J. Gen. Virol.* (1988) 69:1531–1574, for a discussion of the various HSV-1 encoded proteins; U.S. Pat. No. 5,171,568 for a discussion of HSV-1 and HSV-2 gB and gD proteins and the genes encoding therefor; Baer et al., *Nature* (1984) 310:207–211, for the identification of protein coding sequences in an EBV genome; and Davison and Scott, *J. Gen. Virol.* (1986) 67:1759–1816, for a review of VZV.)

Polynucleotide sequences encoding proteins from the hepatitis family of viruses, including hepatitis A virus (HAV), hepatitis B virus (HBV), hepatitis C virus (HCV), the delta hepatitis virus (HDV), hepatitis B virus (HEV) and hepatitis G virus (HGV), can also be conveniently used in the techniques described herein. By way of example, the viral genomic sequence of HCV is known, as are methods for obtaining the sequence. See, e.g., International Publication Nos. WO 89/04669; WO 90/11089; and WO 90/14436. The HCV genome encodes several viral proteins, including E1 (also known as E) and E2 (also known as E2/NSI). (See, Houghton et al., *Hepatology* (1991) 14:381–388, for a discussion of HCV proteins, including E1 and E2.) The sequences encoding each of these proteins, as well as antigenic fragments thereof, will find use in the present system. Similarly, the coding sequence for the 6-antigen from HDV is known (see, e.g., U.S. Pat. No. 5,378,814) and this sequence can also be conveniently used in the present system. Additionally, antigens derived from HBV, such as the core antigen, the surface antigen, sAg, as well as the presurface sequences, preS1 and preS2 (formerly called preS), as well as combinations of the above, such as sAg/preS1, sAg/preS2, sAg/preS1/preS2, and preS1/preS2, will find use herein. See, e.g., "HBV Vaccines—from the laboratory to license: a case study" in Mackett, M. and Williamson, J. D., *Human Vaccines and Vaccination*, pp. 159–176, for a discussion of HBV structure; Beames et al., *J. Virol.* (1995) 69:6833–6838, Birnbaum et al., *J. Virol.* (1990) 64:3319–3330; and Zhou et al., *J. Virol.* (1991) 65:5457–5464.

Polynucleotide sequences encoding proteins derived from other viruses will also find use in the expression systems, such as without limitation, proteins from members of the families Picomaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae (e.g., HTLV-I; HTLV-II; HIV-I (also known as HTLV-III, LAV, ARV, hTLR, etc.)), including but not limited to antigens from the isolates $HIV_{IIIb}$, $HIV_{SF2}$, $HIV_{LAV}$, $HIV_{LAI}$, $HIV_{MN}$); HIV-$1_{CM235}$, HIV-$1_{US4}$; HIV-2; simian immunodeficiency virus (SIV) among others. See, e.g. Virology, 3rd Edition (W. K. Joklik ed. 1988); *Fundamental Virology,* 2nd Edition (B. N. Fields and D. M. Knipe, eds. 1991), for a description of these and other viruses.

For example, the invention may be used in expression constructs to express genes encoding the gp120 envelope protein from any of the above HIV isolates. The gp120 sequences for a multitude of HIV-1 and HIV-2 isolates, including members of the various genetic subtypes of HIV, are known and reported (see, e.g., Myers et al., Los Alamos Database, Los Alamos National Laboratory, Los Alamos, N. Mex. (1992); Myers et al., *Human Retroviruses and Aids,* 1990, Los Alamos, N. Mex.: Los Alamos National Laboratory; and Modrow et al., *J. Virol.* (1987) 61:570–578, for a comparison of the envelope gene sequences of a variety of HIV isolates) and sequences derived from any of these isolates will find use in the present methods. Furthermore, the invention is equally applicable to other immunogenic proteins derived from any of the various HIV isolates, including any of the various envelope proteins such as gp160 and gp41, gag antigens such as p24gag and p55gag, as well as proteins derived from the pol region.

The present invention will also find use in expression constructs for the expression of influenza virus proteins. Specifically, the envelope glycoproteins HA and NA of influenza A are of particular interest for generating an immune response. Numerous HA subtypes of influenza A have been identified (Kawaoka et al., *Virology* (1990) 179:759–767; Webster et at., "Antigenic variation among type A influenza viruses," p. 127–168. In: P. Palese and D. W. Kingsbury (ed.), *Genetics of influenza viruses*. Springer-Verlag, New York). Thus, the gene sequences encoding proteins derived from any of these isolates can also be used in the recombinant production techniques described herein.

Furthermore, the fragments described herein provide a means for producing proteins useful for treating a variety of malignant cancers. For example, the system of the present invention can be used to produce a variety of tumor antigens which in turn may be used to mount both humoral and cell-mediated immune responses to particular proteins specific to the cancer in question, such as an activated oncogene, a fetal antigen, or an activation marker. Such tumor antigens include any of the various MAGEs (melanoma associated antigen E), including MAGE 1, 2, 3, 4, etc. (Boon, T. *Scientific American* (March 1993):82–89); any of the various tyrosinases; MART 1 (melanoma antigen recognized by T cells), mutant ras; mutant p53; p97 melanoma antigen; CEA (carcinoembryonic antigen), among others.

It is readily apparent that the subject invention can be used to produce a variety of proteins useful for the prevention, treatment and/or diagnosis of a wide variety of diseases.

Polynucleotide sequences coding for the above-described molecules can be obtained using recombinant methods, such as by screening cDNA and genomic libraries from cells expressing the gene, or by deriving the gene from a vector known to include the same. Furthermore, the desired gene can be isolated directly from cells and tissues containing the same, using standard techniques, such as phenol extraction and PCR of cDNA or genomic DNA. See, e.g., Sambrook et al., supra, for a description of techniques used to obtain and isolate DNA. The gene of interest can also be produced synthetically, rather than cloned. The nucleotide sequence can be designed with the appropriate codons for the particular amino acid sequence desired. In general, one will select preferred codons for the intended host in which the sequence will be expressed. The complete sequence may be assembled from overlapping oligonucleotides prepared by standard methods and assembled into a complete coding sequence. See, e.g., Edge, *Nature* (1981) 292:756; Nambair et al., *Science* (1984) 223:1299; Jay et al., *J. Biol. Chem.* (1984) 259:6311.

Markers and amplifiers can also be employed in the subject expression systems. A variety of markers are known which are useful in selecting for transformed cell lines and generally comprise a gene whose expression confers a selectable phenotype on transformed cells when the cells are grown in an appropriate selective medium. Such markers for mammalian cell lines include, for example, the bacterial xanthine-guanine phosporibosyl transferase gene, which can be selected for in medium containing mycophenolic acid and xanthine (Mulligan et al. (1981) *Proc. Natl. Acad. Sci. USA* 78:2072–2076), and the aminoglycoside phosphotransferase gene (specifying a protein that inactivates the antibacterial action of neomycin/kanamycin derivatives), which can be selected for using medium containing neomycin derivatives such as G418 which are normally toxic to mammalian cells (Colbere-Garapin et al. (1981) *J. Mol. Biol.* 150:1–14). Useful markers for other expression systems, are well known to those of skill in the art. These and other selectable markers can be obtained from commercially available plasmids, using techniques well known in the art. See, e.g., Sambrook et al., supra.

Expression can also be amplified by placing an amplifiable gene, such as the mouse dihydrofolate reductase (dhfr) gene adjacent to the coding sequence. Cells can then be selected for methotrexate resistance in dhfr-deficient cells. See, e.g. Urlaub et al. (1980) *Proc. Natl. Acad. Sci. USA* 77:4216–4220; Ringold et al. (1981) *J. Mol. and Appl. Genet.* 1:165–175. Constructs which include both markers and amplifiers will also find use in the subject expression vectors, such as any of the various EMCV-DHFR/Neo constructs described in, e.g., U.S. Pat. No. 6,096,505, incorporated herein by reference in its entirety.

Transcription termination and polyadenylation sequences may also be present, located 3' to the translation stop codon for the coding sequence. Examples of transcription terminator/polyadenylation signals include, but are not limited to, those derived from SV40, as described in Sambrook et al., supra, as well as a bovine growth hormone terminator sequence.

Also present in the expression constructs of the invention will be a promoter region. The promoter may be the homologous hCMV IE1 promoter normally associated with the intact, full-length Intron A sequence from which the fragment is derived, a heterologous CMV IE1 promoter (e.g., from a different CMV strain), or even a non-CMV IE1 promoter. The choice of promoter will depend on the cell type used for expression and is readily determined by one of skill in the art. For example, typical promoters for mammalian cell expression include the SV40 early promoter, a CMV promoter as described above, the mouse mammary tumor virus LTR promoter, the adenovirus major late promoter (Ad MLP), the RSV promoter, the SRa promoter, the herpes simplex virus promoter, tissue-specific promoters, among others. One particular promoter used in the constructs described herein is a promoter derived from the hCMV IE1 enhancer/promoter region depicted in FIG. 2, such as approximately nucleotide positions 460 to 1264 of FIG. 2, or functional portions of this region. Other nonviral promoters, such as a promoter derived from the murine metallothionein gene, will also find use for mammalian expression. Insect cell expression systems, typically Baculovirus systems, will generally include a polyhedrin promoter. Promoters for use in bacterial systems include promoter sequences derived from sugar metabolizing enzymes, such as galactose, lactose (lac) (Chang et al., *Nature* (1977) 198:1056), and maltose, promoter sequences derived from biosynthetic enzymes such as tryptophan (trp) (Goeddel et al., *Nuc. Acids Res.* (1980) 8:4057; Yelverton et al., *Nucl. Acids Res.* (1981) 9:731; U.S. Pat. No. 4,738,921; EPO Publication Nos. 036,776 and 121,775), the b-lactamase (bla) promoter system (Weissmann (1981) "The cloning of interferon and other mistakes" in *Interferon* 3 (ed. 1. Gresser)), bacteriophage lambda PL (Shimatake et al., *Nature* (1981) 292:128), the T5 promoter (U.S. Pat. No. 4,689,406), hybrid promoters such as tac, a hybrid trp-lac promoter (Amann et al., *Gene* (1983) 25:167; de Boer et al., *Proc. Natl. Acad. Sci.* (1983) 80:21). Promoters useful in yeast expression systems include, for example, promoters from sequences encoding enzymes in the metabolic pathway such as alcohol dehydrogenase (ADH) (EPO Publication No. 284,044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO Publication No. 329,203) promoters. Other promoters for use in such systems include a promoter derived from the yeast PHO5 gene, encoding acid phosphatase (Myanohara et al., *Proc. Natl. Acad. Sci. USA* (1983) 80:1), as well as synthetic such as a promoter formed by the fusion of UAS sequences of one yeast promoter with the transcription activation region of another yeast promoter, creating a synthetic hybrid promoter. Examples of such hybrid promoters include the ADH regulatory sequence linked to the GAP transcription activation region (U.S. Pat. Nos. 4,876,197 and 4,880,734), as well as promoters which consist of the regulatory sequences of either the ADH2, GAL4, GAL10, or PHO5 genes, combined with the transcriptional activation region of a glycolytic enzyme gene such as GAP or PyK (EPO Publication No. 164,556). These and other promoters can be obtained from commercially available plasmids, using techniques well known in the art. See, e.g., Sambrook et al., supra.

An expression vector is constructed so that the particular coding sequence is located in the vector with the Intron A fragment and the appropriate regulatory sequences, the positioning and orientation of the coding sequence with respect to the control sequences being such that the coding sequence is transcribed under the "control" of the control sequences (i.e., RNA polymerase which binds to the DNA molecule at the promoter transcribes the coding sequence). Modification of the sequences encoding the molecule of interest may be desirable to achieve this end. For example, in some cases it may be necessary to modify the sequence so that it can be attached to the promoter and other control sequences in the appropriate orientation; i.e., to maintain the reading frame. The promoter sequence and other regulatory sequences may be ligated to the coding sequence prior to insertion into a vector. Alternatively, the coding sequence can be cloned directly into an expression vector which already contains the Intron A fragment and an appropriate restriction site.

It may also be desirable to produce mutants or analogs of the gene of interest.

Mutants or analogs of the polypeptide of interest may be prepared by the deletion of a portion of the sequence encoding the polypeptide of interest, by insertion of a sequence, and/or by substitution of one or more nucleotides within the sequence. Techniques for modifying nucleotide sequences, such as site-directed mutagenesis, and the like, are well known to those skilled in the art. See, e.g., Sambrook et al., supra; Kunkel, T. A. (1985) *Proc. Natl. Acad. Sci. USA* (1985) 82:448; Geisselsoder et al. (1987) *BioTechniques* 5:786; Zoller and Smith (1983) *Methods Enzymol.* 100:468; Dalbie-McFarland et al. (1982) *Proc. Natl. Acad. Sci USA* 79:6409.

Once the expression constructs are assembled, they can be used in a wide variety of systems, including insect, mammalian, bacterial, viral and yeast expression systems, all well known in the art. Nucleic acid molecules comprising nucleotide sequences of interest can be stably integrated into a host cell genome or maintained on a stable episomal element in a suitable host cell using various gene delivery techniques well known in the art. See, e.g., U.S. Pat. No. 5,399,346.

For example, insect cell expression systems, such as baculovirus systems, are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit). Similarly, bacterial and mammalian cell expression systems are well known in the art and described in, e.g., Sambrook et al., supra. Yeast expression systems are also known in the art and described in, e.g., *Yeast Genetic Engineering* (Barr et al., eds., 1989) Butterworths, London.

A number of appropriate host cells for use with the above systems are also known. For example, mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human embryonic kidney cells, human hepatocellular carcinoma cells (e.g., Hep G2), Madin-Darby bovine kidney ("MDBK") cells, as well as others. Similarly, bacterial hosts such as *E. coli, Bacillus subtilis,* and *Streptococcus spp.*, will find use with the present expression constructs. Yeast hosts useful in the present invention include inter alia, *Saccharomyces cerevisiae, Candida albicams, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica.* Insect cells for use with baculovirus expression vectors include, inter alia, *Aedes aegypti, Autographa californica, Bombyx mori, Drosophila melanogaster, Spodoptera frugiperda*, and *Trichoplusia ni*.

A wide variety of methods can be used to deliver the expression constructs to cells. Such methods include DEAE dextran-mediated transfection, calcium phosphate precipitation, polylysine- or polyornithine-mediated transfection, or precipitation using other insoluble inorganic salts, such as strontium phosphate, aluminum silicates including bentonite and kaolin, chromic oxide, magnesium silicate, talc, and the like. Other useful methods of transfection include electroporation, sonoporation, protoplast fusion, liposomes, peptoid delivery, or microinjection. See, e.g., Sambrook et al., supra, for a discussion of techniques for transforming cells of interest.

For example, the expression constructs can be packaged in liposomes prior to delivery to the cells. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, *Biochim. Biophys. Acta.* (1991) 17:1–17; Straubinger et al., in *Methods of Enzymology* (1983), Vol. 101, pp. 512–527.

Liposomal preparations for use with the present invention include cationic (positively charged), anionic (negatively charged) and neutral preparations, with cationic liposomes particularly preferred. Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner et al., *Proc. Natl. Acad. Sci. USA* (1987) 84:7413–7416). Other commercially available lipids include transfectace (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* (1978) 75:4194–4198; PCT Publication No. WO 90/11092 for a description of the synthesis of DOTAP (1,2-bis(oleoyloxy)-3-(trimethylammonio)propane) liposomes. The various liposome-nucleic acid complexes are prepared using methods known in the art. See, e.g., Straubinger et al., in METHODS OF IMMUNOLOGY (1983), Vol. 101, pp. 512–527; Szoka et al., *Proc. Natl. Acad. Sci. USA* (1978) 75:4194–4198; Papahadjopoulos et al., *Biochim. Biophys. Acta* (1975) 394:483; Wilson et al., *Cell* (1979) 17:77); Deamer and Bangham, *Biochim. Biophys. Acta* (1976) 443:629; Ostro et al., *Biochem. Biophys. Res. Commun.* (1977) 76:836; Fraley et al., *Proc. Natl. Acad. Sci. USA* (1979) 76:3348); Enoch and Strittmatter, *Proc. Natl. Acad. Sci. USA* (1979) 76: 145); Fraley et al., *J. Biol. Chem.* (1980) 255:10431; Szoka and Papahadjopoulos, *Proc. Natl. Acad. Sci. USA* (1978) 75:145; and Schaefer-Ridder et al., *Science* (1982) 215:166.

The DNA can also be delivered in cochleate lipid compositions similar to those described by Papahadjopoulos et al., *Biochem. Biophys. Acta*. (1975) 394:483–491. See, also, U.S. Pat. Nos. 4,663,161 and 4,871,488.

Depending on the expression system and host selected, the molecules are produced by growing host cells transformed by an expression vector described above under conditions whereby the protein is expressed. The expressed protein is then isolated from the host cells and purified. If the expression system secretes the protein into growth media, the product can be purified directly from the media. If it is not secreted, it can be isolated from cell lysates. The selection of the appropriate growth conditions and recovery methods are within the skill of the art. For example, once expressed, the product may be isolated and purified by any number of techniques, well known in the art, including: chromatography, e.g., HPLC, affinity chromatography, ion exchange chromatography, size-exclusion, etc.; electrophoresis; density gradient centrifugation; solvent extraction, or the like. See, e.g., *Protein Purification Principles and Practice*, 2nd edition (Robert K. Scopes ed. 1987); and *Protein Purification Methods, a Practical Approach* (E. L. V. Harris and S. Angal, eds. 1990).

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. Genes can be delivered either directly to the vertebrate subject or, alternatively, delivered ex vivo, to cells derived from the subject and the cells reimplanted in the subject.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman, *BioTechniques* (1989) 7:980–990; Miller, A. D., *Human Gene Therapy* (1990) 1:5–14; Scarpa et al., *Virology* (1991) 180:849–852; Burns et al., *Proc. Natl. Acad. Sci. USA* (1993) 90:8033–8037; and Boris-Lawrie and Temin, *Cur. Opin. Genet. Develop.* (1993) 3:102–109. Briefly, retroviral gene delivery vehicles of the present invention may be readily constructed from a wide variety of retroviruses, including for example, B, C, and D type retroviruses as well as spumaviruses and lentiviruses such as FIV, HIV, HIV-1, HIV-2 and SIV (see RNA Tumor Viruses, Second Edition, Cold Spring Harbor Laboratory, 1985). Such retroviruses may be readily obtained from depositories or collections such as the American Type Culture Collection ("ATCC"; 10801 University Blvd., Manassas, Va. 20110-2209), or isolated from known sources using commonly available techniques.

A number of adenovirus vectors have also been described. Unlike retroviruses which integrate into the host genome, adenoviruses persist extrachromosomally thus minimizing the risks associated with insertional mutagenesis (Haj-Ahmad and Graham, *J. Virol.* (1986) 57:267–274; Bett et al., *J. Virol.* (1993) 67:5911–5921; Mittereder et al., *Human Gene Therapy* (1994) 5:717–729; Seth et al., *J. Virol.* (1994) 68:933–940; Barr et al., *Gene Therapy* (1994) 1:51–58; Berkner, K. L. *BioTechniques* (1988) 6:616–629; and Rich et al., *Human Gene Therapy* (1993) 4:461–476).

Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., *Molec. Cell. Biol.* (1988) 8:3988–3996; Vincent et al., *Vaccines* 90 (1990) (Cold Spring Harbor Laboratory Press); Carter, B. J. *Current Opinion in Biotechnology* (1992) 3:533–539; Muzyczka, N. *Current Topics in Microbiol. and Immunol.* (1992) 158:97–129; Kotin, R. M. *Human Gene Therapy* (1994) 5:793–801; Shelling and Smith, *Gene Therapy* (1994) 1:165–169; and Zhou et al., *J. Exp. Med.* (1994) 179:1867–1875.

Molecular conjugate vectors, such as the adenovirus chimeric vectors described in Michael et al., *J. Biol. Chem.* (1993) 268:6866–6869 and Wagner et al., *Proc. Natl. Acad. Sci. USA* (1992) 89:6099–6103, can also be used for gene delivery.

Members of the *Alphavirus* genus, such as but not limited to vectors derived from the Sindbis, Semnliki Forest viruses and VEE, will also find use as viral vectors for delivering the gene of interest. For a description of Sinbus-virus derived vectors useful for the practice of the instant methods, see, Dubensky et al., *J. Virol.* (1996) 70:508–519, and International Publication Nos. WO 95/07995 and WO 96/17072.

The expression constructs of the present invention can also be delivered without a viral vector. For example, the construct can be delivered directly, or packaged in liposomes prior to delivery to the subject or to cells derived therefrom, as described above.

The expression constructs may also be encapsulated, adsorbed to, or associated with, particulate carriers. Such carriers present multiple copies of a selected molecule to the immune system and promote trapping and retention of molecules in local lymph nodes. The particles can be phagocytosed by macrophages and can enhance antigen presentation through cytokine release. Examples of particulate carriers include those derived from polymethyl methacrylate polymers, as well as microparticles derived from poly (lactides) and poly(lactide-co-glycolides), known as PLG. See, e.g., Jeffery et al., *Pharm. Res.* (1993) 10:362–368; and McGee et al., *J. Microencap.* (1996).

Furthermore, other particulate systems and polymers can be used for the in vivo or ex vivo delivery of the expression constructs. For example, polymers such as polylysine, polyarginine, polyormithine, spermine, spermidine, as well as conjugates of these molecules, are useful for transferring a nucleic acid of interest. Similarly, DEAE dextran-mediated transfection, calcium phosphate precipitation or precipitation using other insoluble inorganic salts, such as strontium phosphate, aluminum silicates including bentonite and kaolin, chromic oxide, magnesium silicate, talc, and the like, will find use with the present system. See, e.g., Felgner, P. L., *Advanced Drug Delivery Reviews* (1990) 5:163–187, for a review of delivery systems useful for gene transfer.

Additionally, biolistic delivery systems employing particulate carriers such as gold and tungsten, are especially useful for delivering the expression constructs of the present invention. The particles are coated with the construct to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744.

Deposits of Strains Useful in Practicing the Invention

A deposit of biologically pure cultures of the following strains was made with the American Type Culture Collection, 10801 University Boulevard, Manassas, Va. The accession number indicated was assigned after successful viability testing, and the requisite fees were paid, made under the provisions of the Budapest Treaty on the International Recognition of the Deposit of Microorganisms for the Purpose of Patent Procedure and the Regulations thereunder (Budapest Treaty). This assures maintenance of viable cultures for a period of thirty (30) years from the date of deposit. The organisms will be made available by the ATCC under the terms of the Budapest Treaty, which assures permanent and unrestricted availability of the progeny to one determined by the U.S. Commissioner of Patents and Trademarks to be entitled thereto according to U.S.C. §122 and the Commissioner's rules pursuant thereto (including 37 C.F.R. §1.12 with particular reference to 886 OG 638). Upon the granting of a patent, all restrictions on the availability to the public of the deposited cultures will be irrevocably removed.

These deposits are provided merely as convenience to those of skill in the art, and are not an admission that a deposit is required under 35 U.S.C. §112. The nucleic acid sequences of these genes, as well as the amino acid sequences of the molecules encoded thereby, are incorporated herein by reference and are controlling in the event of any conflict with the description herein. A license may be required to make, use, or sell the deposited materials, and no such license is hereby granted.

| Plasmid | Deposit Date | ATCC No. |
|---------|--------------|----------|
| pCON3 | Sep. 27, 2000 | PTA-2504 |

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Restriction and modifying enzymes, as well as other reagents for DNA manipulations were purchased from commercial sources, and used according to the manufacturers' directions. In the cloning of DNA fragments, except where noted, all DNA manipulations were done according to standard procedures. See, e.g., Sambrook et al., supra.

EXAMPLE 1

Production of Expression Constructs Including Intron A Fragments

A series of 13 expression constructs were made which deleted from between 54 and 688 nucleotides from within the core region of Intron A, bounded by the splice donor and branch point sites. The expression constructs were linked to the firefly (*Photinus pyralis*) luciferase gene or to a codon-optimized HIV p55gag gene (Zur Megede et al., *J. Virol.* (2000) 74:2628–2635.)

The initial deletion of Intron A was prepared by means of substituting a 778 base pair NsiI-SalI fragment from plasmid pCMVkmLuc (International Publication No. WO 98/06437) with a synthetic oligonucleotide (FIG. 1B) that restored the last 80 nucleotides of Intron A (with optimized branch point and polypyrimidine tract sequences as shown in FIG. 1B), together with Exon 2 of the 5'-UTR (nucleotides 821–834 of FIG. 1A). The resulting construct contained a 688 bp deletion from Intron A and is shown in FIG. 1A. The resulting expression plasmid, pCON3, contains the hCMV enhancer/promoter region with a 130 bp Intron A fragment. The final sequence of the intron in pCON3 is shown in FIG. 1C.

Twelve additional Intron A deletion constructs were made by progressive deletion within plasmid pCMVII (U.S. Pat. No. 6,096,505) in either the 5'-3' direction from the unique NsiI site toward the unique HpaI site, or in the 3'-5' direction from the HpaI site toward the NsiI site (see, FIG. 3 and Table 1). Following the restriction enzyme digests, the plasmids were treated with T4 DNA polymerase and excess dNTPs. Resulting blunt-ended vector fragments were gel-purified and self-ligated. As shown in FIG. 3, these constructs included deletions within the intron ranging from 54 to 663 base pairs in length. To generate expression vectors carrying the resulting intron modifications, the NdeI-SalI fragment from the truncation plasmids was substituted into plasmid pCMVkmLuc digested with NdeI and SalI. Of these constructs, selected ones were digested with SalI-XbaI to generate recipient vector fragments for the insertion of the codon-optimized HIV p55gag gene obtained by digestion of plasmid pCMVkm2.GAGmod.SF2 (Zur Megede et al., *J. Virol.* (2000) 74:2628–2635).

TABLE 1

| Digest | Deletion Length (bp) | NT. deleted from Intron A (following digest, blunting, religation) |
|--------|---------------------|---------------------------------------------------------------------|
| NsiI-Ce/II | 70 | 47–116 |
| NsiI-XcmI | 113 | 47–159 |
| NsiI-PflmI | 150 | 47–196 |
| NsiI-MroI | 345 | 47–391 |
| NsiI-BfrI | 578 | 47–624 |
| NsiI-PvuII | 609 | 47–655 |
| NsiI-HpaI | 663 | 47–709 |
| HpaI-PvuII | 54 | 656–709 |
| HpaI-BrfI | 80 | 630–709 |
| HpaI-MroII | 314 | 395–709 |
| HpaI-PflmI | 516 | 193–709 |
| HpaI-Ce/II | 590 | 119–709 |

EXAMPLE 2

Expression of a Heterologous Coding Sequence Using Intron A Fragments 293 (ATTC Accession No. CRL-1573) and RD (ATTC Accession No. CCL-136) cells were grown in DMEM medium supplemented with fetal calf serum (10% v/v).

Fourteen hours prior to transfection, $2 \times 10^5$ cells/well were seeded into 6 well plates. Transient transfection was done using 2 μg of the vector DNA described above, per well using 12 μg of Fugene 6 (Roche Molecular Biochemicals, Indianapolis, Ind.) per supplier instructions in 6 replicate wells per construct. Forty-eight hours post-transfection, cell lysates were analyzed for reporter gene expression. HIV p55gag expression was evaluated by means of a p24 antigen ELISA (Coulter, Miami, Fla.). Geometric mean titers across each plate (construct) were calculated.

Transient transfection of 293 cells and evaluation of luciferase expression indicated that nearly all of these derivatives expressed as well as or better than the parent vector, pCMVkm-Luciferase containing the full-length Intron A sequence. The constructs containing the two largest intron deletions (pCon3, ΔHpaI-CelII) showed the greatest enhancement, approximately two-fold greater than the parent vector (FIG. 4).

To further evaluate the effect on expression of a smaller intron, the entire sequence of Intron A was substituted with the 126 base pair Intron I from the rabbit globin gene (RβG-IVSI). FIG. 5A shows the wild-type rabbit β-globin gene sequence used. In vitro analysis of p55gag expression indicated that the wild-type construct expressed up to approximately 1.8 times higher than the parent vector, pCMVkm-Luciferase (FIG. 6). The wild-type sequences for the splice donor, branch point and polyY tract of RβG-IVSI are suboptimal relative to the consensus sequences for these elements. Therefore, the construct containing RβG-IVSI was modified such that these sequence elements were optimized. FIG. 5B shows the optimized rabbit β-globin gene sequence used, termed RβG-OPTI. Analysis of this construct showed approximately 4 times higher p55gag expression as compared to the parent vector in vitro (FIG. 6).

All 14 modified-intron constructs were analyzed for efficiency of RNA transcript splicing by RT-PCR. For RNA transcript analysis, 293 cells were transiently transfected and then lysed using RNAstat 60 (Tel-Test B, Inc., Friendswood, Tex.) to yield total cell RNA. Extracted RNA was digested with RQ1-Dnase (Promega Corp, Madison, Wis.) and subjected to RT-PCR using the GeneAmp RNA PCR kit (Roche Molecular Biochemicals, Indianapolis, KN. PCR spanning the region of the intron was done using an upstream primer in exon 1 of the 5' UTR [primer "KBT-162"; seq. CGCT-GTTTGACCTCCATA (SEQ ID NO:7)] and a downstream primer from the luciferase reporter gene [primer "KBT-163"; seq. GTTGAGCAATTCACGTTCAT (SEQ ID NO: 8)]; a control PCR of actin transcripts was also performed for each RNA preparation. All of the mutants spliced efficiently, within the sensitivity of the assay, as no products of lengths predicted for unspliced messages were detected.

EXAMPLE 3

Nucleic Acid Immunization Using the Intron A Fragment

In order to test the ability of the Intron A fragments to direct transcription in vivo, Balb/C mice in groups of 6 animals (Charles River Co., Wilmington, Mass.) were immunized once bilaterally in the tibialis anterior muscle with 5 μg of naked vector DNA per injection site (prepared endotoxin-free [Qiagen, Inc., Valencia, Calif.] and formulated in normal saline). Three- and six-week post-immunization bleeds were analyzed by ELISA for anti-HIV p55gag antibody as described in Zur Megede et al., J. Virol. (2000) 74:2628–2635.

Figure 7:
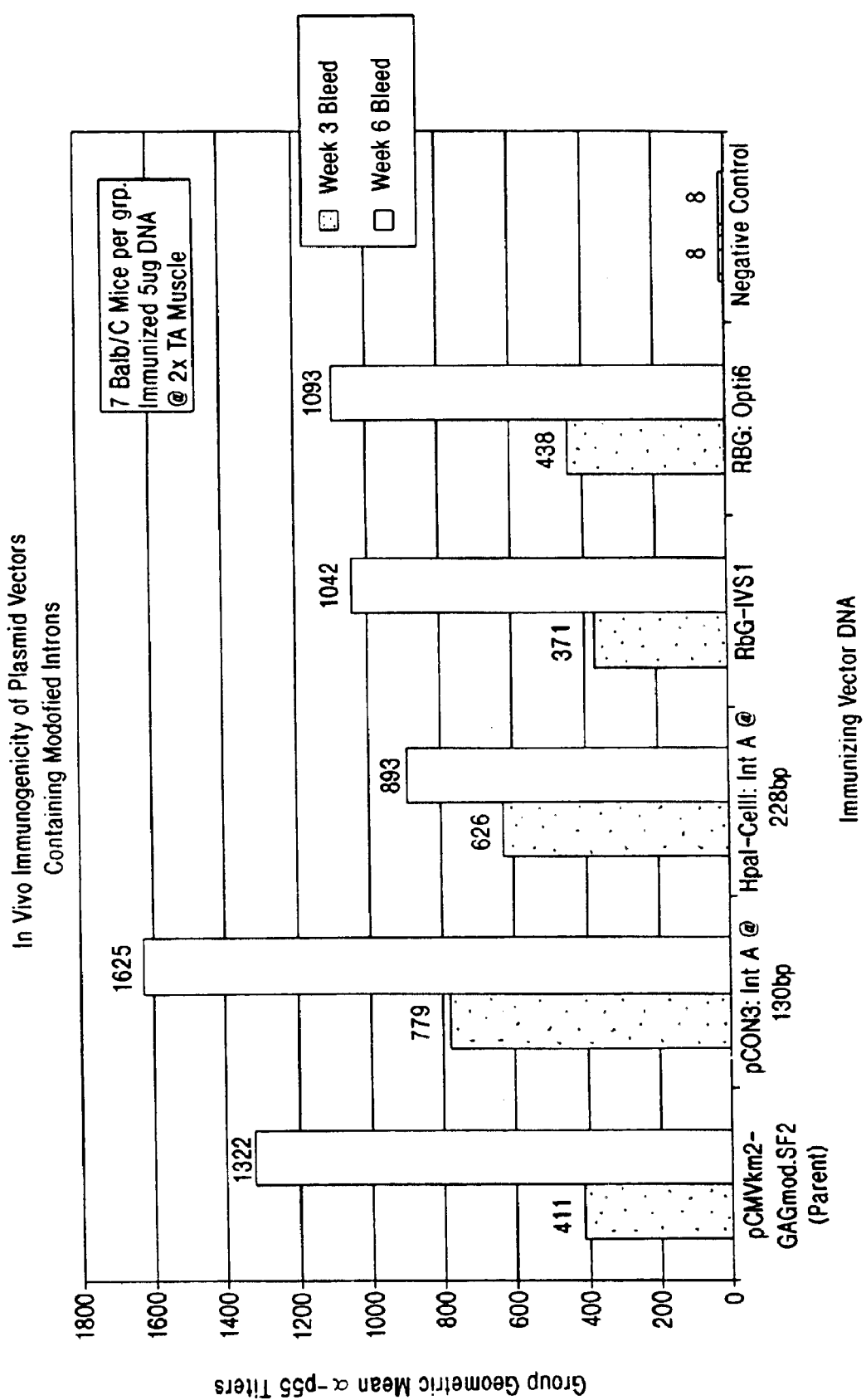
FIG. 7 depicts anti-p55gag titers from mice immunized with various constructs including the Intron A fragment, as described in the examples.

The constructs evaluated are shown in FIG. 7. Variable immunogenicites were seen after a single immunization (see, FIG. 7). Significantly, the pCON3 vector which deleted approximately 85% of Intron A yielded higher geometric mean titers than the parent pCMVkm2.GAGmod.SF2 vector (FIG. 7). At three weeks post-immunization, the titer was approximately twice that of the parent vector though this fell off by six weeks post-injection.

Accordingly, novel hCMV Intron A fragments and methods of using the same have been disclosed. From the foregoing, it will be appreciated that, although specific embodiments of the invention have been described herein for purposes of illustration, various modifications may be made without deviating from the spirit and scope of the appended claims.

What is claimed is:

1. A human cytomegalovirus (hCMV) Intron A fragment, wherein said fragment has an internal deletion of at least 10 nucleotides of the full-length Intron A sequence and comprises: (a) the contiguous sequence of nucleotides found at positions 1–25 of SEQ ID NO: 1, and (b) the contiguous sequence of nucleotides found at positions 775–820 of SEQ ID NO: 1, wherein when said fragment is present in an expression construct, the expression construct directs the transcription of a coding sequence present in the construct at levels equal to, or greater than, those levels achieved by an expression construct that includes a corresponding intact, full-length Intron A sequence.

2. The Intron A fragment of claim 1, wherein when said fragment is present in an expression construct, the expression construct directs the transcription of a coding sequence present in the construct at levels at least two-fold greater than those levels achieved by an expression construct that includes a corresponding intact, full-length Intron A sequence.

3. A recombinant expression construct effective in directing the transcription of a selected coding sequence, said expression construct comprising:
   (a) a coding sequence;
   (b) control elements that are operably linked to said coding sequence, wherein said control elements comprise the Intron A fragment of claim 1,
   whereby said coding sequence can be transcribed and translated in a host cell.

4. A host cell comprising the recombinant expression construct of claim 3.

5. The recombinant expression construct of claim 3, wherein said control elements further comprise a promoter selected from the group consisting of a simian virus 40 (SV40) early promoter, a cytomegalovirus (CMV) promoter, a mouse mammary tumor virus long terminal repeat promoter, an adenovirus major late promoter, a rous sarcoma virus (RSV) promoter, a SRα promoter, and a herpes simplex virus promoter.

6. The Intron A fragment of claim 1, wherein said fragment comprises: the contiguous sequence of nucleotides found at positions 1–51 of SEQ ID NO:1, and (b) the contiguous sequence of nucleotides found at positions 741–820 of SEQ ID NO:1, wherein when said fragment is present in an expression construct, the expression construct directs the transcription of a coding sequence present in the construct at levels equal to, or greater than those levels achieved by an expression construct that includes a corresponding intact, full-length Intron A sequence.

7. The Intron A fragment of claim 6, wherein when said fragment is present in an expression construct, the expression construct directs the transcription of a coding sequence present in the construct at levels at least two-fold greater than those levels achieved by an expression construct that includes a corresponding intact, full-length Intron A sequence.

8. The Intron A fragment of claim 6, wherein said fragment comprises in 5' to 3' order: the sequence of nucleotides 1–51 of SEQ ID NO:1, linked to nucleotides 741–820 of SEQ ID NO:1.

9. A recombinant expression construct effective in directing the transcription of a selected coding sequence, said expression construct comprising:
   (a) a coding sequence;
   (b) control elements that are operably linked to said coding sequence, wherein said control elements comprise the Intron A fragment of claim 8, whereby said coding sequence can be transcribed and translated in a host cell.

10. A host cell comprising the recombinant expression construct of claim 9.

11. A human cytomegalovirus (hCMV) Intron A fragment, wherein said fragment comprises the nucleotide sequence of SEQ ID NO:3, or a nucleotide sequence with at least 95% sequence identity thereto, wherein when said fragment is present in an expression construct, the expression construct directs the transcription of a coding sequence present in the construct at levels equal to, or greater than, those levels achieved by an expression construct that includes a corresponding intact, full-length Intron A sequence.

12. The Intron A fragment of claim 11, wherein said fragment consists of the nucleotide sequence of SEQ ID NO:3.

13. A recombinant expression construct effective in directing the transcription of a selected coding sequence, said expression construct comprising:
   (a) a coding sequence;
   (b) control elements that are operably linked to said coding sequence, wherein said control elements comprise the Intron A fragment of claim 12,
   whereby said coding sequence can be transcribed and translated in a host cell.

14. A host cell comprising the recombinant expression construct of claim 13.

15. The recombinant expression construct of claim 13, wherein said control elements further comprise the hCMV immediate-early (IE1) enhancer/promoter region found at nucleotide positions 460 to 1264 of SEQ ID NO:4, and said control elements further comprise the sequence of nucleotides at positions 821–834 of SEQ ID NO:1.

16. A host cell comprising the recombinant expression construct of claim 15.

17. A human cytomegalovirus (hCMV) Intron A fragment, wherein said fragment comprises in 5' to 3' order: a sequence of nucleotides having at least 95% sequence identity to the contiguous sequence of nucleotides found at positions 1–51 of SEQ ID NO:1 linked to a sequence of nucleotides having at least 95% sequence identity to the contiguous sequence of nucleotides found at positions 741–820 of SEQ ID NO: 1, wherein when said fragment is present in an expression construct, the expression construct directs the transcription of a coding sequence present in the construct at levels equal to, or greater than, those levels achieved by an expression construct that includes a corresponding intact, full-length Intron A sequence.

* * * * *

SEQUENCE LISTING

<160> NUMBER OF SEQ ID NOS: 8

<210> SEQ ID NO 1
<211> LENGTH: 834
<212> TYPE: DNA
<213> ORGANISM: Artificial Sequence
<220> FEATURE:
<223> OTHER INFORMATION: Description of Artificial Sequence: full
      length intron A

<400> SEQUENCE: 1

```
gtaagtaccg cctatagact ctataggcac acccctttgg ctcttatgca tgctatactg      60
tttttggctt ggggcctata caccccgct ccttatgcta taggtgatgg tatagcttag     120
cctataggtg tgggttattg accattattg accactcccc tattggtgac gatactttcc     180
attactaatc cataacatgg ctctttgcca caactatctc tattggctat atgccaatac     240
tctgtccttc agagactgac acggactctg tatttttaca ggatggggtc catttattat     300
ttacaaattc acatatacaa caacgccgtc ccccgtgccc gcagttttta ttaaacatag     360
```

```
cgtgggatct ccgacatctc gggtacgtgt tccggacatg ggctcttctc cggtagcggc    420
ggagcttcca catccgagcc ctggtcccat gcctccagcg gctcatggtc gctcggcagc    480
tccttgctcc taacagtgga ggccagactt aggcacagca caatgcccac caccaccagt    540
gtgccgcaca aggccgtggc ggtagggtat gtgtctgaaa atgagctcgg agattgggct    600
cgcaccgtga cgcagatgga agacttaagg cagcggcaga agaagatgca ggcagctgag    660
ttgttgtatt ctgataagag tcagaggtaa ctcccgttgc ggtgctgtta acggtggagg    720
gcagtgtagt ctgagcagta ctcgttgctg ccgcgcgcgc caccagacat aatagctgac    780
agactaacag actgttcctt tccatgggtc ttttctgcag tcaccgtcgt cgac          834

<210> SEQ ID NO 2
<211> LENGTH: 100
<212> TYPE: DNA
<213> ORGANISM: Artificial Sequence
<220> FEATURE:
<223> OTHER INFORMATION: Description of Artificial Sequence: Synthetic
      oligo for substitution of nucleotides 52-740 of
      Intron A

<400> SEQUENCE: 2
atgcatctcg ttgctgccgc gcgcgccacc agacataatc gctgacacac tgacagactg    60
ttcctttcct tttttttttt ttgcagtcac cgtcgtcgac                          100

<210> SEQ ID NO 3
<211> LENGTH: 145
<212> TYPE: DNA
<213> ORGANISM: Artificial Sequence
<220> FEATURE:
<223> OTHER INFORMATION: Description of Artificial Sequence: Deletion
      mutant pCON3 Intron

<400> SEQUENCE: 3
gtaagtaccg cctatagact ctataggcac accccttttgg ctcttatgca tctcgttgct    60
gccgcgcgcg ccaccagaca taatcgctga cacactgaca gactgttcct ttccttttt     120 ttttttgca gtcaccgtcg tcgac                                            145

<210> SEQ ID NO 4
<211> LENGTH: 2170
<212> TYPE: DNA
<213> ORGANISM: Artificial Sequence
<220> FEATURE:
<223> OTHER INFORMATION: Description of Artificial Sequence: major
      immediate-early gene of hCMV

<400> SEQUENCE: 4
ctgcagtgaa taataaaatg tgtgtttgtc cgaaatacgc gttttgagat ttctgtcgcc    60
gactaaattc atgtcgcgcg atagtggtgt ttatcgccga tagagatggc gatattggaa    120
aaatcgatat ttgaaaatat ggcatattga aaatgtcgcc gatgtgagtt tctgtgtaac    180
tgatatcgcc attttccaa aagtgatttt tgggcatacg cgatatctgg cgatacggct    240
tatatcgttt acggggatg gcgatagacg actttggcga cttgggcgat tctgtgtgtc    300
gcaaatatcg cagtttcgat ataggtgaca gacgatatga ggctatatcg ccgatagagg    360
cgacatcaag ctggcacatg gccaatgcat atcgatctat acattgaatc aatattggca    420
attagccata ttagtcattg gttatatagc ataaatcaat attggctatt ggccattgca    480
tacgttgtat ctatatcata atatgtacat ttatattggc tcatgtccaa tatgaccgcc    540
```

```
atgttgacat tgattattga ctagttatta atagtaatca attacggggt cattagttca    600
tagcccatat atggagttcc gcgttacata acttacggta aatggcccgc ctcgtgaccg    660
cccaacgacc cccgcccatt gacgtcaata atgacgtatg ttcccatagt aacgccaata    720
gggactttcc attgacgtca atgggtggag tatttacggt aaactgccca cttggcagta    780
catcaagtgt atcatatgcc aagtccggcc ccctattgac gtcaatgacg gtaaatggcc    840
cgcctggcat tatgcccagt acatgacctt acgggacttt cctacttggc agtacatcta    900
cgtattagtc atcgctatta ccatggtgat gcggttttgg cagtacacca atgggcgtgg    960
atagcggttt gactcacggg gatttccaag tctccacccc attgacgtca atgggagttt   1020
gttttggcac caaaatcaac gggactttcc aaaatgtcgt aataacccccg ccccgttgac  1080
gcaaatgggc ggtaggcgtg tacggtggga ggtctatata agcagagctc gtttagtgaa   1140
ccgtcagatc gcctggagac gccatccacg ctgttttgac ctccatagaa gacaccggga   1200
ccgatccagc ctccgcggcc gggaacggtg cattggaacg cggattcccc gtgccaagag   1260
tgacgtaagt accgcctata gactctatag cacaccccct ttggctctta tgcatgctat   1320
actgtttttg gcttggggcc tatacacccc cgctccttat gctataggtg atggtatagc   1380
ttagcctata ggtgtgggtt attgaccatt attgaccact cccctattgg tgacgatact   1440
ttccattact aatccataac atggctcttt gccacaacta tctctattgg ctatatgcca   1500
atactctgtc cttcagagac tgacacggac tctgtatttt tacaggatgg ggtcccattt   1560
attatttaca aattcacata tacaacaacg ccgtccccg tgcccgcagt ttttattaaa    1620
catagcgtgg gatctccacg cgaatctcgg gtacgtgttc cggacatggg ctcttctccg   1680
gtagcggcgg agcttccaca tccgagccct ggtcccatgc ctccagcggc tcatggtcgc   1740
tcggcagctc cttgctccta acagtggagg ccagacttag gcacagcaca atgcccacca   1800
ccaccagtgt gccgcacaag gccgtggcgg tagggtatgt gtctgaaaat gagctcggag   1860
attgggctcg caccgtgacg cagatggaag acttaaggca gcggcagaag aagatgcagg   1920
cagctgagtt gttgtattct gataagagtc agaggtaact cccgttgcgg tgctgttaac   1980
ggtggagggc agtgtagtct gagcagtact cgttgctgcc gcgcgcgcca ccagacataa   2040
tagctgacag actaacagac tgttcctttc catgggtctt ttctgcagtc accgtccttg   2100
acacgatgga gtcctctgcc aagagaaaga tggaccctga taatcctgac gagggccctt   2160
cctccaagtt                                                          2170
```

<210> SEQ ID NO 5
<211> LENGTH: 126
<212> TYPE: DNA
<213> ORGANISM: Artificial Sequence
<220> FEATURE:
<223> OTHER INFORMATION: Description of Artificial Sequence: wild type
      rabbit beta-globin

<400> SEQUENCE: 5

```
gttggtatcc ttttttacagc acaacttaat gagacagata gaaactggtc ttgtagaaac     60
agagtagtcg cctgcttttc tgccaggtgc tgacttctct cccctgggct gttttcattt    120
tctcag                                                                126
```

<210> SEQ ID NO 6
<211> LENGTH: 127
<212> TYPE: DNA
<213> ORGANISM: Artificial Sequence
<220> FEATURE:

-continued

```
<223> OTHER INFORMATION: Description of Artificial Sequence:  optimized
      rabbit beta-globin

<400> SEQUENCE: 6
gtaagtatcc tttttacagc acaacttaat gagacagata gaaactggtc ttgtagaaac      60
agagtagtcg cctgcttttc tgccaggtac taacttctct cccctctcct cttttctttt    120
tctgcag                                                              127

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence:  primer
      KBT-162

<400> SEQUENCE: 7
cgctgttttg acctccata                                                  19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:  primer
      KBT-163

<400> SEQUENCE: 8
gttgagcaat tcacgttcat                                                 20
```